(12) United States Patent
Farkas et al.

(10) Patent No.: US 11,653,874 B2
(45) Date of Patent: May 23, 2023

(54) METHOD AND SYSTEM FOR CHARACTERIZING TISSUE IN THREE DIMENSIONS USING MULTIMODE OPTICAL MEASUREMENTS

(71) Applicant: ACCELERITAS CORPORATION, Sherman Oaks, CA (US)

(72) Inventors: Daniel L. Farkas, Beverly Hills, CA (US); Fartash Vasefi, Sherman Oaks, CA (US); Nicholas MacKinnon, Vancouver (CA)

(73) Assignee: ACCELERITAS CORPORATION, Sherman Oaks, CA (US)

( * ) Notice: Subject to any disclaimer, the term of this patent is extended or adjusted under 35 U.S.C. 154(b) by 224 days.

(21) Appl. No.: 14/821,672

(22) Filed: Aug. 7, 2015

(65) Prior Publication Data
US 2015/0374276 A1    Dec. 31, 2015

Related U.S. Application Data

(63) Continuation-in-part of application No. 14/815,691, filed on Jul. 31, 2015, now abandoned, which is a
(Continued)

(51) Int. Cl.
*A61B 5/00* (2006.01)
*A61B 5/1455* (2006.01)
*A61B 5/145* (2006.01)

(52) U.S. Cl.
CPC .......... *A61B 5/443* (2013.01); *A61B 5/14558* (2013.01); *A61B 5/444* (2013.01);
(Continued)

(58) Field of Classification Search
CPC ....... A61B 5/00; A61B 5/443; A61B 5/14558; A61B 5/444; A61B 5/14546; A61B 5/14551; A61B 2576/02; G01N 21/00
See application file for complete search history.

(56) References Cited

U.S. PATENT DOCUMENTS 7,289,211 B1 * 10/2007 Walsh, Jr. ............ A61B 5/0086
356/369
7,945,077 B2    5/2011 Demos
(Continued)

FOREIGN PATENT DOCUMENTS

EP    1196081    1/2011
EP    2951301    12/2015
(Continued)

OTHER PUBLICATIONS

D'Alessandro, Brian, and Atam P. Dhawan. "3-D volume reconstruction of skin lesions for melanin and blood volume estimation and lesion severity analysis." IEEE transactions on medical imaging 31.11 (2012): 2083-2092 (Year: 2012).*
(Continued)

*Primary Examiner* — Sean D Mattson
(74) *Attorney, Agent, or Firm* — ArentFox Schiff LLP

(57) ABSTRACT

A surface of the tissue is illuminated with light having a known wavelength spectrum capable of materially penetrating the tissue. The light remitted from the tissue in response to the illumination is separated into at least two distinguishable polarization components. The intensity of the illumination light remitted from the tissue is measured over a hyperspectral range of wavelengths for the at least two distinguishable polarization components. Based on the preceding measurements and a degree of linear polarization of the remitted light, data representative of the three-dimensional location and one or more characteristics of an abnormal portion of the tissue are produced. Further, the masking effect of melanin may be eliminated to obtain accurate estimations of an anomaly.

6 Claims, 23 Drawing Sheets

Related U.S. Application Data continuation of application No. PCT/US2014/014330, filed on Jan. 31, 2014.

(60) Provisional application No. 61/759,910, filed on Feb. 1, 2013.

(52) U.S. Cl.
CPC ....... *A61B 5/14546* (2013.01); *A61B 5/14551* (2013.01); *A61B 2576/02* (2013.01)

(56) References Cited

U.S. PATENT DOCUMENTS

| | | | |
|---|---|---|---|
| 2005/0228366 A1 | 10/2005 | Kessler | |
| 2009/0137908 A1* | 5/2009 | Patwardhan | A61B 5/0059 600/476 |
| 2009/0326383 A1* | 12/2009 | Barnes | A61B 5/0059 600/476 |
| 2010/0042004 A1* | 2/2010 | Dhawan | A61B 5/0059 600/476 |

FOREIGN PATENT DOCUMENTS

| | | |
|---|---|---|
| WO | 01/01854 A2 | 1/2011 |
| WO | 2014121152 A1 | 8/2014 |

OTHER PUBLICATIONS

PCT IPER and Written Opinion, in PCT/US14/052399, dated Mar. 10, 2016.
First Examiner's Report dated Jan. 13, 2020 for corresponding CA application No. 2900138.
Extended European Search Report dated Sep. 29, 2016 in European Patent Application No. 14746421.8.
International Search Report and Written Opinion issued for Int'l Appl No. PCT/US2014/014330, Int'l Filing Date Jan. 31, 2014, dated May 29, 2014.
International Preliminary Report on Patentability for Int'l Appl. No. PCT/US2014/014330, Int'l Filing Date Jan. 31, 2014, dated Aug. 4, 2015.

* cited by examiner

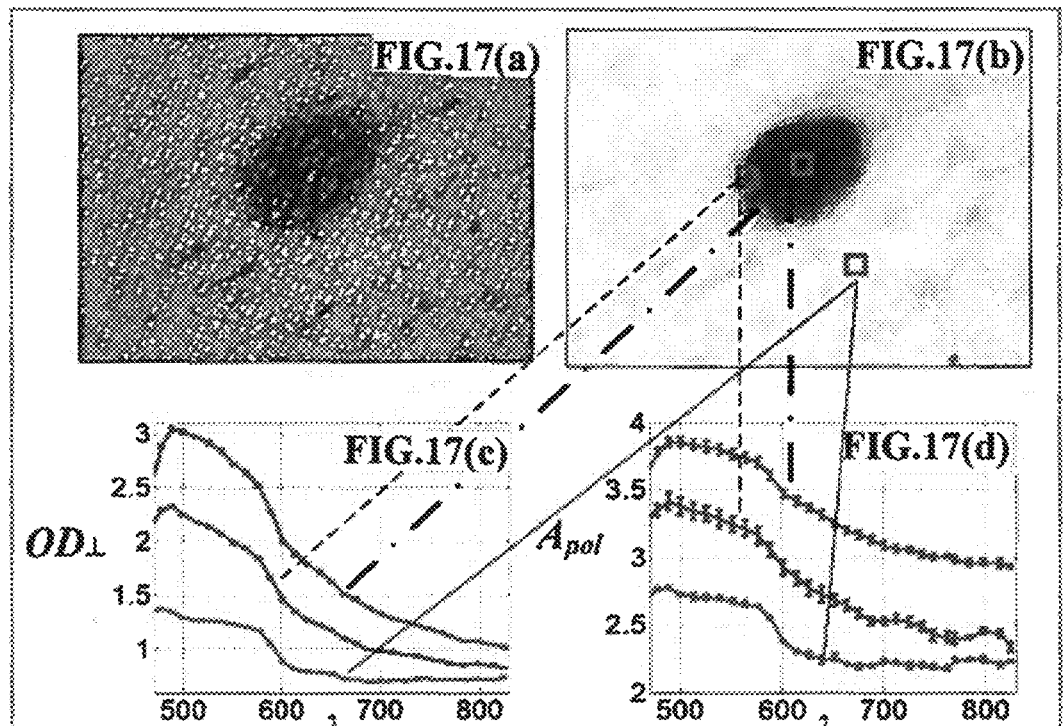
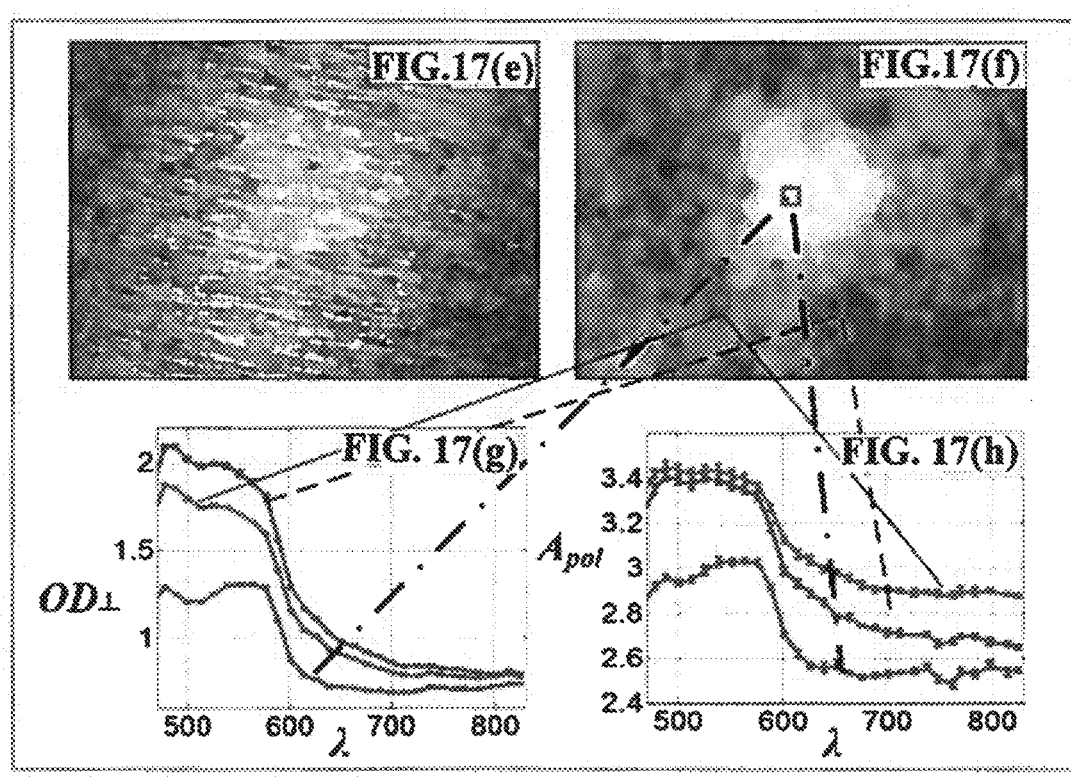

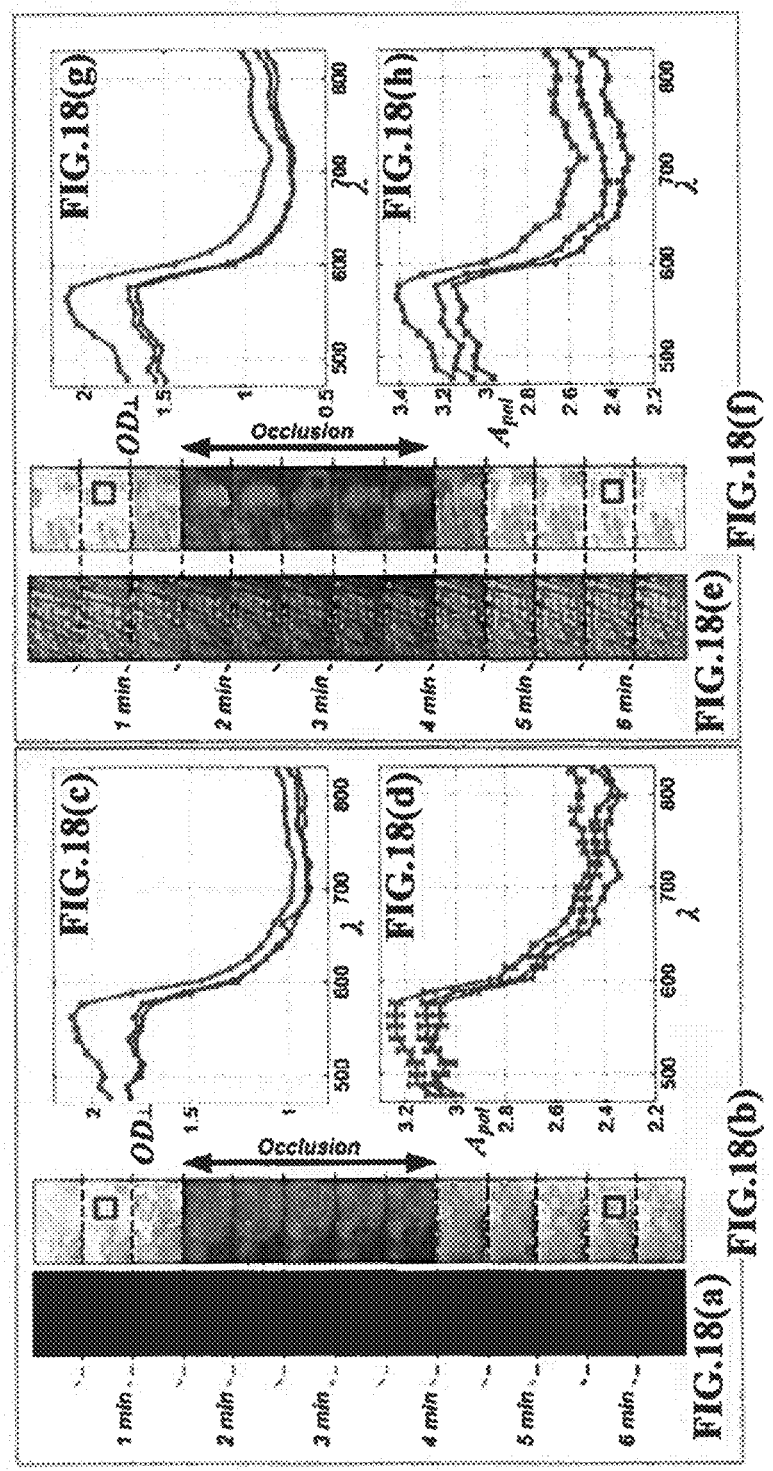

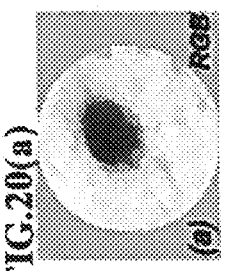
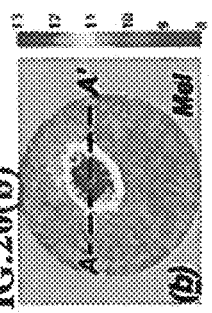
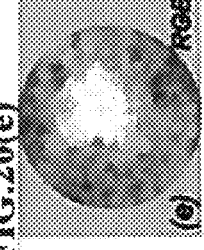
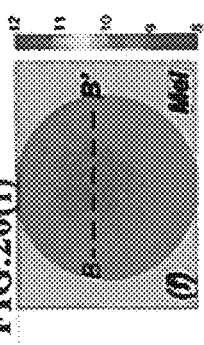
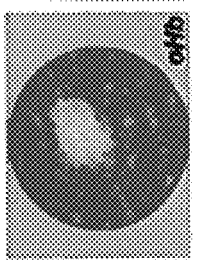
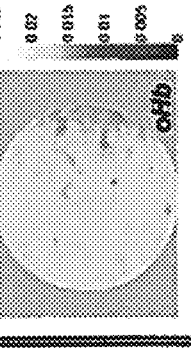
FIG. 20(a) – FIG. 20(h)

METHOD AND SYSTEM FOR CHARACTERIZING TISSUE IN THREE DIMENSIONS USING MULTIMODE OPTICAL MEASUREMENTS

RELATED APPLICATIONS

This application is a continuation-in-part of U.S. application Ser. No. 14/815,691, filed Jul. 31, 2015, which is a continuation of international application Serial No. PCT/US2014/014330, filed Jan. 31, 2014 and designating the U.S., which claims the benefit under 35 U.S.C. § 119(e) of U.S. patent application Ser. No. 61/759,910, filed Feb. 1, 2013, all of which are incorporated by reference herein in their entireties.

BACKGROUND OF THE INVENTION

Melanoma is a serious and challenging disease. It is an increasingly lethal form of skin cancer, especially when detected in later stages. Melanoma risk during a lifetime increased from 1:1500 in 1935 to 1:58 in 2009, and is still the fastest growing cancer both in the U.S. and worldwide. The National Cancer Center has estimated that 76,250 patients will be diagnosed with melanoma of the skin in 2012 and that 9,180, or more than one patient per hour, will die.

Survival rates strongly favor early diagnosis, ranging from 98.2% for early, primary site detection to at best 15.1% for late or metastasized detection, during a recent 5 year study. As much as about $2.4 billion has been spent in the United States each year on melanoma treatment.

Treatment costs average $1,800 for early and $180,000 for late detection. This indicates significant cost savings by diagnosing melanoma earlier. Despite great effort worldwide, no significant advancements in treatment have occurred. Therefore early detection is by far the most effective means of fighting this disease that accounts for 75% of all skin cancer deaths.

The present common standard in melanoma patient care is a dermatologists' visual examination, such as the ABCDE procedure or revised 7-point checklist in which the practitioner looks for abnormalities in shape, size and color.

Around 2 million biopsies are performed annually to detect melanoma, and the vast majority of these (over 80%) are benign. An alternative approach to enhance ABCDE evaluation can include a dermoscope with (low power) magnification or specific illumination or both.

More recently, more complex imaging or sensing systems that quantify anatomical and physiological information about skin have been developed, such as MoleMate™ (MedX, Toronto, Canada). MoleMate is a 4-color, light emitting diode ("LED") based non-invasive melanoma screening device that employs Spectrophotometric Intracutaneous Analysis ("SIA"). SIA scans are used to gather information about a patient's suspicious moles and lesions by imaging pigment, collagen, and blood directly under the mole or lesion.

Other systems, such as the MelaFind® and Verisante Aura™ devices, use "blackbox" methods based on statistical classifiers. (MelaFind is a registered trademark of Mela Sciences Inc.; Verisante Aura is claimed as a trademark by The BC Cancer Agency and the University of British Columbia) Although all of these optical systems provide high sensitivity, they have not achieved the desired level of specificity in diagnosis. Typically, the blackbox approach assumes there is an optical signature difference between normal and cancerous tissues and addresses differentiation between these tissue states by using statistical classifiers and training-based discrimination functions. Unfortunately many systems employing these methods have shown reductions in performance as the studies move from smaller to larger populations.

A telling example is the specificity reduction in the MelaFind® device from 84% reported in 2001 compared to results in the 9.5% to 11% range in 2011. The MelaFind® device data shows unavoidable rates of false-positives and false-negatives. The MelaFind® device data was not validated and the device cannot be used for lesions with foreign material present such as dirt, ink or splinters, or with skin erosion, ulcers or bleeding and others defects. Some private practice dermatologists find that they cannot justify its use.

As reflected in such data the statistical classification approach is encountering fundamental barriers to success as promising clinical devices fail when they are evaluated in larger studies. A key problem is that in order to adequately validate these statistical models large numbers of patients must have biopsy confirmed measurements to develop these models or else resulting diagnostic algorithms will have poor performance. This means large and thus expensive clinical trials are required.

Another more fundamental limitation is that the "black box approach" is only indirectly linked to tissue physiology. The limited biological plausibility has kept clinicians and dermatologists from embracing this method. When considered with the modest improvement of specificity from the current dermatologist examination specificity of 3% to the 10% to 13% range of specificity of such devices, it is difficult to justify their adoption. This is especially true when both the change of procedure and the equipment expense are considered. There is an unmet need for a method to diagnose melanoma with sufficient biological plausibility for clinicians to understand the relationship to the underlying physiology that may guide treatment and follow-up.

It is clear that such attempts to achieve early detection have shown disappointing reductions in specificity when clinical trials proceed from smaller to larger study populations. Increasing the specificity of dermatological instruments for detection of disease will lead to early diagnosis of melanoma, reducing the risk of cancer development and mortality, improving skin healthcare, and making the medical treatment of melanoma less expensive, faster, and more available to a wider range of population including underserved areas. There exists an unmet need for such an increase in specificity.

Obtaining the depth of the melanoma lesion is of cardinal importance in successful early diagnosis. Some attempts to diagnose melanoma have tried to provide some level of depth related information, but this depth information is generally not presented quantitatively; rather, it is characterized as "seeing under the skin" of melanoma lesions.

One method that does provide depth information is high resolution confocal microscopy such as that performed by the VivaScope confocal microscope (a registered trademark of Caliber Imaging & Diagnostics, Rochester, N.Y.). It takes a microscopic image of a shallow depth of skin lesion (~700 µm) and small field of view (FOV ~1 mm×1 mm), which is then analyzed by a dermal pathologist to detect melanoma or other skin cancers. These devices are very expensive, and the interpretation of the information requires the skills of a pathologist. There is still an unmet a need for a device that provides simple-to-interpret depth information about a melanoma lesion at a reasonable cost.

Some commercial products and many research devices for skin analysis attempt to define tissue characteristics based on spectral measurements followed by feature extraction algorithms and statistical analysis Gutkowcz-Krusin, D., Elbaum, M. Jacobs, A., Keem, S., Kopf, A. W., et al. Precision of automatic measurements of pigmented skin lesion parameters with a MelaFind multispectral digital dermoscope., *Melanoma Res*, 10, 563-70 (2000). These statistical classifiers are used to decide whether a tissue has a particular pathology, but there is little information that can be directly related to the tissue biology providing a model that does not distinguish between correlation and causation. This makes it difficult to evaluate the algorithm for the biological plausibility that usually engenders clinical confidence in a medical device Bergstrom, K. G. MelaFind was approved by FDA; where does it fit in dermatology?, *J Drug Dermatol*, 11, 420-422 (2012).

In skin studies, using SIAscopy, the limited multi-wavelength measurements appear to be inadequate for the light-tissue model being applied, Moncrieff, M., Cotton, S., Claridge, E., & Hall, P. Spectrophotometric intracutaneous analysis: a new technique for imaging pigmented skin lesions., *Br J Dermatol* 146, 448-57 (2002), because the results do not adequately correlate with pathology, Terstappen, K., Suurktüla, M., Hallberg, H., Ericson M. B., & Wennberg, A. M., Poor correlation between spectrophotometric intracutaneous analysis and histopathology in melanoma and nonmelanoma lesions., *J. Biomed Opt*, 18, 061223 (2013). A simple test of biological plausibility, where measured results are compared to known published, physiologically reasonable values, might lead to better algorithms and more accurately reflect the underlying biology. Instead, instances of results that are to be contrary to physiological expectations have been observed, such as local variation in oxygen saturation under perfectly normal pigmented nevi. Vyas, S. Banerjee, A., & Burlina P. Estimating physiological skin parameters from hyperspectral signatures., *J. Biomed Opt* 18, 057008 (2013), data showing that people of different races have different regional oxygen saturation, Yudovsky, D. & Pilon, L. Retrieving skin properties from in vivo spectral reflectance measurements., *J Biophotonics*, 4, 305-314 (2011), or that collagen fluorescence is different under pigmented and non-pigmented regions. Na, R., Stender, I. M., Henriksen, M., & Wulf H. C. Autofluorescence of human skin is age-related after correction for skin pigmentation and redness., *J. Invest Derm*, 116, 536-540 (2001).

Instead of statistical classifiers, which tend to be indirectly linked to physiological features, it is desirable to develop technology that elucidates physiologically important structures and processes both faster and more accurately, so clinicians may detect, quantify and manage treatment of skin problems including melanoma or basal cell carcinoma, chronic wounds like diabetic or pressure ulcers resulting from a compromised dermis, burn wounds, as well as fungal or bacterial infections.

There are a variety of algorithms that have been used to quantify skin chromophores that employ tissue light-transport models. Various forward models can be employed ranging from Beer-Lambert, Martinez L. A non-invasive spectral reflectance method for mapping blood oxygen saturation in wounds. *Proc. Of the 31st Applied Imagery Pattern Recognition Workshop*, 112-116 (2002) and Kubelka-Munk, Vyas, S., Banerjee, A., & Burlina, P. Estimating physiological skin parameters from hyperspectral signatures., *J. Biomed Opt*, 18 057008 (2013), to the approximation of the Radiative Transfer Eq. (RTE), Yudovsky, D & Pilon, L. Retrieving skin properties from in vivo spectral reflectance measurements, *J. Biophotonics*, 4, 305-314 (2011). The governing Eq. for light transfer through tissue can be solved using Monte Carlo, Zeng, H., MacAulay, C. E., Palcic, B., & McLean, D. I., Monte Carlo modeling of tissue autofluoresence measurement and imaging *SPIE OE/LASE '94*, 94-104 (1994), Wang, L., Jacques, S. L., & Zheng, L. MCML—Monte Carlo modeling of light transport in multi-layered tissues. *Comput Meth Prog Bio* 47, 131-146 (1995), Tsumura, N., Kawabuchi, M., Haneishi, H., & Miyake, Y. Mapping pigmentation in human skin from a multi-channel visible spectrum image by inverse optical scattering technique, *J. Imaging Sci, Technol*, 45, 444-450 (2001), finite element Katika K. M., & Pilon, L. Steady-state directional diffuse reflectance and fluorescence of human skin., *Appl Optics*, 45 4174-4183 (2006)], or discrete methods Guo, Z., & Kim, K, "Ultrafast-Laser-Radiation Transfer in Heterogeneous Tissues with the Discrete-Ordinates Method" *Appl Optics* 42 2897-2905 (2003). These approaches vary in terms of computational speed. Real time algorithms usually are associated with relatively simple models such as ratiometric analysis Kapsokalyvas, D., Bruscino, N., Alfieri, D., de Giorgi, V., Cannarozzo G., et al Spectral morphological analysis of skin lesions with a polarization multispectral dermoscope., *Opt Express*, 21 4826-4840 (2013), Diebele, I., A. Bekina, A. Derjabo, J. Kapostinsh, I. Kuzmina, and J. Spigulis. "Analysis of skin basalioma and melanoma by multispectral imaging." In Proc. SPIE, vol. 8427, p. 842732. 2012. Real time computation (30 ms to 1000 ms) is ideal for extracting high resolution skin chromophore two-dimensional maps from three-dimensional spectral image stacks with millions of voxels. These rapid quantification algorithms range from ratiometric calculations of skin reflectance maps at various wavelengths to Beer-Lambert, Attas, M., Hewo, M., Payette, J., Posthumus, T., Sowa, M., et al. Visualization of cutaneous hemoglobin oxygeneation and skin hydration using near-infrared spectroscopic imaging., *Skin Res Technol*, 7, 238-245 (2001) or two-flux Kubelka-Munk models (up to few minutes) for homogenous turbid media, Anderson, R. R., & Parrish, J. A., The optics of human skin. *J Invest Derm* 77, 13-19 (1981), MacKinnon, N. B., Vasefi, F., Gussakovsky, E., Bearman, G. H., Chave, R., et al. In vivo skin chromophore mapping using a multimode imaging dermoscope (SkinSpec™), *Proc. SPIE*, 8587, 85870U (2013). Alternatively, models of light propagation can accommodate heterogeneity by incorporating two or more layers. This typically increases complexity by enabling prediction of layer thicknesses as well as chromophore concentrations for each specific layer Saager, R. B., Truong, A., Cuccia, D. J., & Durkin, A. J., Method for depth-resolved quantitation of optical properties in layered media using spatially modulated quantitative spectroscopy, *J. Biomed Opt*, 16, 077002 (2011), Yudovsky, D., & Durkin, A. J. Spatial frequency domain spectroscopy of two layer media *J. Biomed Opt*, 16 107005 (2011). The complex geometry of skin requires computationally intensive non-linear regression (e.g. Levenberg-Marquardt Zonios, G., Bykowski, J., & Kollias, N. Skin melanin, hemoglobin, and light scattering properties can be quantitatively assessed in vivo using diffuse reflectance spectroscopy., *J Invest Dermatol*, 117(6), 1452-1457 (2001), to fit the measured spectral signature with the estimated spectral signature derived from the related forward model.

In the past, optical imaging has been applied to the research and clinical challenges involved in understanding, detecting and treating skin cancer including melanoma, using spectral imaging systems ranging from the microscopic to the macroscopic Kirkwood, J. M., Farkas, D. L., Chakraborty, A., Dyer, K. F., Tweardy, D. J., et al. Systemic interferon-treatment Stat3 inactivation in melanoma precursor lesions., *Mol Med,* 5, 11-20, (1999), Jacques, S. L., McAuliffe, D. J. The melanosome: threshold temperature for explosive vaporization and internal absorption coefficient during pulsed laser irradiation. *Photochem. Photobiol,* 53, 769-775 (1991), Yang, P., Farkas, D. L., Kirkwood, J. M., Abernathy, J. L., Edington, H. D., et al Macroscopic spectral imaging and gene expression analysis of the early stages of melanoma., *Mol Med,* 5, 785-794 (1999); Farkas, D. L. & Becker, D., Applications of spectral imaging: detection and analysis of human melanoma and its precursors. *Pig Cell Res,* 14, 2-8 (2001), Valesky, M., Spang, A. J., Fisher, G. W., Farkas, D. L. & Becker, D. Non-invasive, dynamic fluorescence imaging of human melanomas reveals that targeted inhibition of bFGF and FGFR-1 blocks tumor growth by inducing melanoma cell apoptosis. *Mol Med,* 8, 103-112 (2002), Pfaff-Smith, A., Kirkwood, J. M., Edington, H. D., Jukic, D. M., Farkas, D. L. et al. Fluorescence imaging analysis of upstream regulators and downstream targets of STAT3 in melanoma precursor lesions obtained from patients before and after systemic low-dose interferon-α treatment., *Mol Imaging,* 2, 65-73 (2003).

However, it has become evident that, even with complex algorithms, misestimation of chromophore concentrations has been reported. High skin melanin content usually leads to over-estimation of deoxy-hemoglobin and total hemoglobin and consequent under-estimation of hemoglobin oxygenation. Recent studies by Kapsokalyvas et al. Spectral morphological analysis of skin lesions with a polarization multispectral dermoscope., *Opt Express,* 21, 4826-4840 (2013) and Kuzmina et al. Towards non-contact skin melanoma selection by multi-spectral imaging analysis, *J Biomed Opt,* 16, 060502 (2011) have shown unusual estimation of hemoglobin contrast affected by melanin hyperpigmentation. The problem persists in complex models where dark-skinned subjects always seem to have much lower oxygenation compared to Caucasian subjects, as presented by Yudovsky et al. Retrieving skin properties from in vivo spectral reflectance measurements, *J Biophotonics,* 4, 305-314 (2011) and Vyas et al. Estimating physiological skin parameters from hyperspectral signatures, *J Biomed Opt,* 18, 057008 (2013). Terstappen et al. Poor correlation between spectrophotometric intracutaneous analysis and histopathology in melanoma and nonmelanoma lesions, *J Biomed Opt,* 18, 061223 (2013) showed a poor correlation between the SIA scans and histopathological findings in pigmented skin lesions, and attributed this error to misrepresentation of melanin and blood content due to high concentrations of melanin disturbing the quantification algorithm determining blood and collagen distributions. This issue is particularly critical for assessment of suspicious lesions for skin cancer (melanoma and non-melanoma) where high melanin content masks accurate determination of hyper vascularization and metabolism, which are both classic indicators of cancer Troyanova, P., Borisova, E., Stoyanova, V. & Avramov, L., Laser-induced autofluoresence spectroscopy of benign and dysplastic nevi and malignant melanoma. *Proc. SPIE,* 6284, 62840K (2005).

Some researchers have tried to minimize the effect of melanin on the misestimation of other chromophores. Kapsokalyvas et al. Spectral morphological analysis of skin lesions with a polarization multispectral dermoscope, *Opt Express,* 21, 4826-4840 (2013) used two color polarization images to extract image contrast related to superficial melanin and employed it to correct the blood map. Another approach used two orthogonal polarization measurements of skin lesions and computed an image based on degree of linear polarization. Jacques, S. L., Ramella-Roman, J. C., & Lee, K. Imaging skin pathology with polarized light, *J Biomed Opt,* 7, 329-340 (2002). Jacques, S. L., Ramella-Roman, J. C., & Lee, K. Imaging superficial tissues with polarized light, *Laser Surg Med,* 26, 119-129 (2000) They predicted that the degree of polarization image would eliminate the effect of superficial melanin which they suggested acts like a neutral density filter, attenuating both the superficial and deeply penetrating light equally. However, they showed in other work that this method was only partially effective in a benign pigmented nevus with a high melanin concentration. Jacques, S. L., Ramella-Roman, J. C., & Lee, K. Imaging superficial tissues with polarized light, *Laser Surg Med,* 26, 119-129 (2000).

Thus, there has been an unmet need for a method of diagnosing melanoma that is linked directly to well understood physiological parameters, that provides sufficient biological plausibility for clinicians, that reduces the need for large and expensive clinical trials, that provides quantitative three dimensional maps of tissue to guide treatment, that can provide sufficient specificity to reduce false positive results and unnecessary treatment and that substantially eliminates the masking effect of melanin in naturally darker skin. The present invention provides methods to provide these and other advantages.

SUMMARY OF THE INVENTION

To overcome the limitations of existing approaches to early diagnosis of melanomas and other tissue abnormalities, a method and system are provided for characterizing a portion of biological tissue.

A disclosed method of characterizing biological tissue comprises illuminating tissue in vivo with multiple wavelengths light having at least two distinguishable polarization modes separating light remitted from said tissue in response to said illumination into at least two distinguishable polarization components forming at least two respective hyperspectral image sets from said at least two distinguishable polarization components and based on the spatial, spectral and polarization characteristics of the at least two respective image sets, determining at least one characteristic of said tissue.

A disclosed system comprises a source of multiple wavelength light configured to illuminate said tissue with a temporal sequence of different wavelengths to produce corresponding images of said hyperspectral image sets.

In both the method and the system, a model of tissue may comprise a theoretically generated model or an empirically generated model. The empirically generated model is based on measurements of illuminated normal tissue or measurements of an illuminated tissue phantom. The characteristics of the abnormal portion of the tissue may be produced by solving an inverse problem based on the model, starting with the measurements of intensity at a plurality of wavelengths and a plurality of polarizations and modifying estimation parameters of the model to produce a solution to the problem that substantially matches the characteristics of the tissue.

In a particular embodiment the method and system the concentration of superficial melanin is separated in order to quantify the deep melanin relative concentration so that oxy-and-deoxy hemoglobin distribution can be accurately asserted so as to provide biologically plausible measurements that can be used to determine lesion anatomy and physiology.

It is to be understood that this summary is provided as a means for generally determining what follows in the drawings and detailed description, and is not intended to limit the scope of the invention. The foregoing and other objects, features, and advantages of the invention will be readily understood upon consideration of the following detailed description taken in conjunction with the accompanying drawings.

BRIEF DESCRIPTION OF THE DRAWINGS

FIG. 17(a) is a colored image of a patch of a subject's skin having melanocytic nevus, illuminated with linearly polarized light having a uniform intensity spectrum from 475 nm to 825 nm and acquired through a parallel linear polarizer.

FIG. 17(b) is a colored image of the skin patch of FIG. 17(a), illuminated as in FIG. 17(a), but acquired through a crossed linear polarizer.

FIG. 17(c) is a graph of crossed-polarization optical density as a function of wavelength for a central (melanocytic nevus core) region, a boundary (halo) region, and a surrounding (normal skin) region of the skin patch.

FIG. 17(d) is a graph of polarized attenuation as a function of wavelength a central (nevus core) region, a boundary (halo) region, and a surrounding (normal skin) region of the skin patch.

FIG. 17(e) is a colored image of a patch of a subject's skin exhibiting vitiligo, illuminated with linearly polarized light having a uniform intensity spectrum from 475 nm to 825 nm and acquired through a parallel linear polarizer.

FIG. 17(f) is a colored image of the skin patch of FIG. 14(a), illuminated as in FIG. 14(a), but acquired through a crossed linear polarizer.

FIG. 17(g) is a graph of crossed-polarization optical density as a function of wavelength for the central region (little or no melanin), the boundary region (some melanin), and the surrounding region (high concentration of melanin) of the skin patch.

FIG. 17(h) is a graph of polarized attenuation as a function of wavelength a central (vitiligo) region, a boundary (halo) region, and a surrounding (normal skin) region of the skin specimen.

FIG. 18(a) is a concatenated sequence of thirteen colored images of a patch of skin on the dorsal side of a finger of a subject experiencing normal blood flow, wherein the images have been taken in thirty-second intervals.

FIG. 18(b) is a concatenated sequence of thirteen colored images of the patch of skin of FIG. 18(a), wherein the images have been taken in thirty-second intervals and the subject's blood flow has been occluded by a cuff around the finger for a one hundred fifty second interval after the beginning and before the end of that sequence.

FIG. 18(c) is a graph of crossed-polarization optical density as a function of wavelength for region I of FIG. 18(b) (before occlusion), region II of FIG. 18(b) (during occlusion), and region III of FIG. 18(b) (after occlusion).

FIG. 18(d) is a graph of the polarization attenuation as a function of wavelength for region I of FIG. 18(b) (before occlusion), region II of FIG. 18(b) (during occlusion), and region III of FIG. 18(b) (after occlusion).

FIG. 18(e) is a concatenated sequence of thirteen colored images of a patch of skin on the volar side of a finger of a subject experiencing normal blood flow, wherein the images have been taken in thirty-second intervals.

FIG. 18(f) is a concatenated sequence of thirteen colored images of the patch of skin of FIG. 18(e), wherein the images have been taken in thirty-second intervals and the subject's blood flow has been occluded by a cuff around the finger for a one hundred fifty second interval after the beginning and before the end of that sequence.

FIG. 18(g) is a graph of crossed-polarization optical density as a function of wavelength for region I of FIG. 16(f) (before occlusion), region II of FIG. 16(f) (during occlusion), and region III of FIG. 16(f) (after occlusion).

FIG. 18(h) is a graph showing the optical density and polarized attenuation for three corresponding images before, during, and after occlusion, for the volar side of the finger.

FIG. 20(a) is a composite (red-green-blue) image of the skin patch of FIGS. 17(a) and 17(b) having a melanocytic nevus.

FIG. 20(b) is a chromophore map of the melanin in the skin patch of FIG. 20(a) derived from the optical density spectra in cross-polarization mode.

FIG. 20(c) is a sequence of chromophore maps of oxy-hemoglobin (oHb), deoxy-hemoglobin (Hb), total hemoglobin (tHb) and an oxygen saturation parameter (OSP) in the skin patch of FIG. 20(a) illustrating how a high melanin concentration is conducive to misestimation of hemoglobin concentrations.

FIG. 20(d) is a sequence of chromophore maps of oxy-hemoglobin (oHb), deoxy-hemoglobin (Hb), total hemoglobin (tHb) and an oxygen saturation parameter (OSP) in the skin patch of FIG. 20(a) derived from a two-chromophore model to correct for the presence of hemoglobin.

FIG. 20(e) is a composite (red-green-blue) image of the skin patch of FIGS. 17(e) and 17(f) exhibiting vitiligo.

FIG. 20(f) is a chromophore map of the melanin in the skin patch of FIG. 20(e) derived from the optical density spectra in cross-polarization mode.

FIG. 20(g) is a sequence of chromophore maps of oxy-hemoglobin (oHb), deoxy-hemoglobin (Hb), total hemoglobin (tHb) and an oxygen saturation parameter (OSP) in the skin patch of FIG. 20(e) illustrating how a high melanin concentration is conducive to misestimation of hemoglobin concentrations.

FIG. 20(h) is a sequence of chromophore maps of oxy-hemoglobin (oHb), deoxy-hemoglobin (Hb), total hemoglobin (tHb) and an oxygen saturation parameter (OSP) in the skin patch of FIG. 20(e) derived from a two-chromophore model and hyperspectral polarized images to correct for the presence of hemoglobin.

DETAILED DESCRIPTION OF EMBODIMENTS OF THE INVENTION

Introduction

Figure 1:
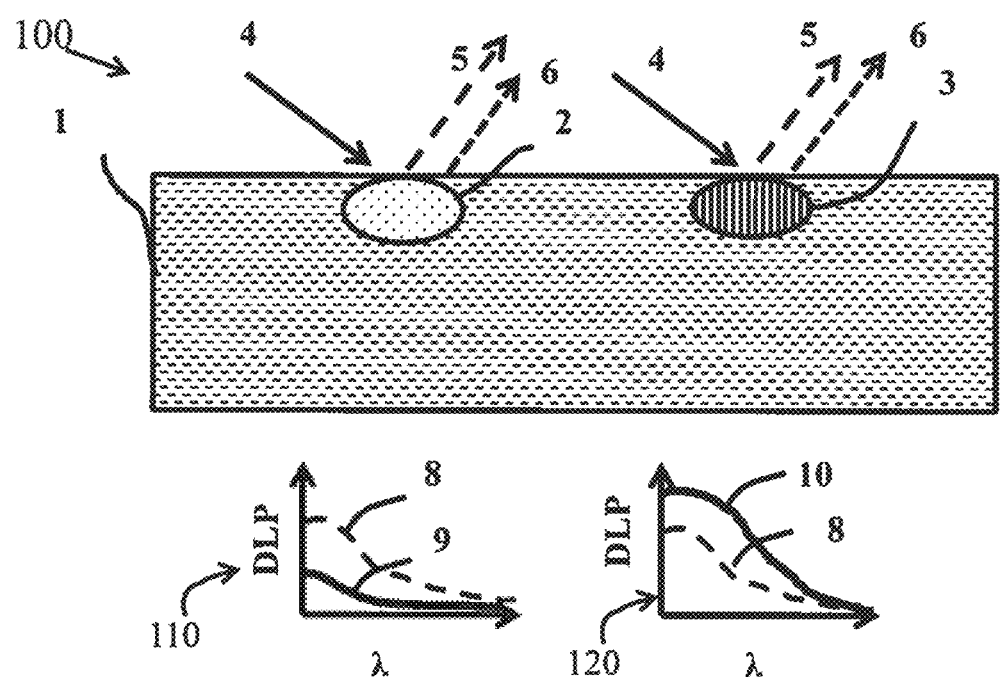
FIG. 1 is a schematic representation of a cross sectional view of biological tissue with two different anomalies at the same depth and graphs illustrating the corresponding degree of linear polarization spectra variation for the respective anomalies.

This disclosure presents preferred embodiments of a system and method that enable the production of a three dimensional map that provides volumetric information about tissue biology from analysis of multimode hyperspectral data cubes. Data cubes are sets of images taken under multiple modalities which can be analyzed. The images for the datasets are captured by a multimode imaging system such as the SkinSpect™ multimode imaging system developed by Spectral Molecular Imaging, Beverly Hills, Calif., which combines hyperspectral, polarization, reflection, scattering, fluorescence and bio-fluorescence imaging modalities. The three-dimensional optical map created from this data provides information to the physicians that helps to diagnose tissue abnormalities with higher precision than with imaging data sets having fewer modalities and combinations thereof.

Hyperspectral imaging is the capture of a sequence of images of a target such as tissue at multiple wavelengths of light that include wavelengths outside the visible spectrum, where each image contains data indicative of the properties of remitted light in a specific narrow wavelength band. "Remitted" light includes reflected and scattered light, and fluorescent, luminescent and bio-luminescent light produced in response to illumination light. The narrow wavelength band can be created by controlling the light illuminating the target, or it can be created by controlling the light emanating from the target.

The sequence of images captured for a hyperspectral image provides reflectance, scattering or other emission data at multiple wavelengths sufficient to reconstruct with reasonable accuracy the reflectance, scattering or other emission spectrum of the target at each image pixel of the target. Typically these spectra will have wavelength data intervals ranging between 1 nm and 50 nm but these intervals may be smaller or larger depending on the nature of the spectrum and the needs of the analysis.

Polarization imaging is the capture of a sequence of images of a target such as tissue, where each image contains data indicative of the polarization properties of the target. Light reflected scattered or otherwise remitted from a tissue can have its polarization properties modified by its passage into or out of a tissue. Polarization images can be created by filtering or otherwise controlling polarization of the light illuminating or remitted from a tissue, or both, and capturing images of light with particular polarization properties.

In accordance with the methods and systems described herein, a computer is used in connection with the acquisition and processing of acquired data to generate an enhanced map, or multi-dimensional data base, of the structural characteristics of the tissue being measured. For example, for the detection of skin cancer, the following reports provided to a clinician automatically and quantitatively: (1) both ABCDE and modified 7-point checklists, (2) three dimensional maps of tissue composition allowing both area and cross-sectional views that can selectively show melanocyte progression, hemoglobin distribution, collagen and elastin abnormalities, and angiogenesis, and (3) surface topology of skin lesions including spatial analysis reports.

Obtaining the depth of a melanoma lesion is of cardinal importance in successful early diagnosis. In order to provide a vigorous link between the data sampled and the physiology of melanoma lesions the invention requires much more comprehensive measurement data than is used in other methods and apparatuses. By obtaining a larger number of wavebands over a wider total bandwidth along with both polarizations, and then applying well developed and understood tissue models to these data, three dimensional distributions of biological features in tissue are obtainable. Melanoma surface lesions are very easy to remove. Lesions with a depth greater than one millimeter quickly become lethal. To provide this depth information, the embodiments disclosed herein use more comprehensive measurement data, and then apply this data to well-developed and understood physiological tissue models to provide quantitative measures of the spatial distribution of biological features in tissue.

As explained in more detail hereafter, the method and system disclosed herein employ data from a combination of optical techniques, including diffuse reflectance spectroscopy, the polarization of light remitted from the tissue, Mie-scattering analysis and tissue fluorescence, luminescence or bio-luminescence in an imaging mode to produce maps of the distribution of tissue features from the surface to depths of up to 2 mm. Polarization filtered fluorescence imaging data is used to determine fluorescence anisotropy analytically to quantify tissue features such as collagen and elastin distribution. Diffuse reflectance hyperspectral imaging is used to quantify hemoglobin, melanin, water and fat distribution, as well as scattering properties of tissue, which can provide information about growth characteristics and cell proliferation. The multimodal nature of the imaging data allows extraction of information to apply to inverse models of tissue optical properties. This method can detect, correct and compensate for data analysis uncertainties that straight spectral imaging or multi-wavelength imaging cannot.

Model-based feature extraction from image data eliminates much of the measurement variability that can plague statistical methods, especially when correlated against associated features or features from neighboring voxels in the image data sets. The direct linkage to underlying tissue characteristics provides the biological plausibility that many clinicians require before adopting a technology. This biological plausibility also makes the method and system more easily testable, using tissue phantoms and appropriate standards to verify accuracy of quantification and ongoing system performance.

A new method and an apparatus are disclosed that use two depth-sensitive techniques: polarization and hyperspectral imaging, to accurately determine the spatial distribution of melanin and hemoglobin oxygenation in a skin lesion. The method and apparatus accurately separate the contribution of superficial melanin in order to quantify the deep melanin relative concentration so that oxy-hemoglobin ("OHb") and deoxy-hemoglobin ("Hb") distribution can be accurately assessed. This provides biologically plausible measurements that can be used to determine the lesion anatomy and physiology. The superficial melanin is primarily found in melanosomes migrating to the skin superficial layer as a part of normal epidermal replacement. Lin, J. Y., & Fisher, D. E. Melanocyte biology and skin pigmentation Nature, 445, 843-850 (2007). The deep melanin is primarily associated with the melanocytes found on the basal layer that separates the epidermis and dermis layers.

A linearly polarized, multi-wavelength light source is used to illuminate the skin while both parallel and perpendicular polarization images of the remitted light are recorded simultaneously by two cameras. This effect is illustrated herein using skin with a melanocytic nevus (high melanin) and skin with vitiligo (low melanin) as well as skin under the influence of venous occlusion (changing hemoglobin) to demonstrate the effectiveness of this method for accurately distinguishing and quantifying hemoglobin and melanin distributions.

Multimode Approach

The method and system for in vivo tissue characterization disclosed herein employ illumination of tissue with hyperspectral, polarized light and spatial measurements of the intensity, spectrum and polarization of light remitted by the tissue in response to the illumination to locate and characterize anomalies in the tissue. Remitted light is intended to refer to light that is spectrally reflected, diffusely reflected or back scattered, or light remitted as fluorescence, luminescence or bio-luminescence, or combinations of the foregoing. Spatial measurements of intensity as a function of wavelength and relative polarization of remitted light have been found to enable construction of three-dimensional functional images of the tissue and to extract the location and character of various anomalies, particularly non-malignant and malignant skin lesions.

1. Hyperspectral Imaging

In accordance with the disclosed embodiments, living tissue is illuminated with a spectrum light preferably in the visible and near-infrared spectrum, typically having material wavelengths ranging from about 400 nanometers to about 1000 nanometers, though the ends of the spectrum used ordinarily are neither sharp nor critically important. The wavelength spectrum over this range may be continuous or discontinuous, even discrete, depending on the particular need. In any case, the illumination light is polarized in a known way. Ordinarily, linear polarization would be used, but other polarizations such as circular or elliptical might be used without departing from the principles of the invention.

The intensity of light remitted from the skin in response to the illumination is measured in a hyperspectral measurement space which is ordinarily two-dimensional. However, it is to be understood that one-dimensional or three-dimensional measurement spaces might be used as well, without departing from the principles of the invention.

2. Polarization Imaging

It has been found that the polarization of remitted light is indicative of the physiologic character of the tissue remitting the light. In particular, it has been found that the polarization of the remitted light relative to the polarization of the illumination light is indicative of the tissue character. This is expressed as the degree of polarization, in particular, the degree of known input polarization in the remitted light. Ordinarily, the input polarization would be linear, and the degree of linear polarization of the remitted light would be measured. In that case, the degree of linear polarization of remitted light $DLP(\lambda)$ at a given point in measurement space may be expressed as a function of wavelength as:

$$DLP(\lambda)=(I_P(\lambda)-I_X(\lambda))/(I_P(\lambda)+I_X(\lambda))$$

where $\lambda$ is the wavelength of light;

$I_P(\lambda)$ is the intensity of linearly polarized remitted light parallel to the input polarization at wavelength $\lambda$; and $I_X(\lambda)$ is the intensity of linearly polarized remitted light perpendicular to the input polarization at wavelength $\lambda$.

More generally it is to be recognized that circularly or elliptically-polarized light might also be used and the degree of polarization would compare the orthogonally polarized light in the remitted light with the remitted light having the input polarization.

3. Fluorescence, Luminescence and Bio-Luminescence Imaging

Tissue fluorescence, luminescence and bio-luminescence remitted in response to input light may also characterize anomalies in the tissue. A comparison of the intensity of remitted fluorescence, luminescence or bio-luminescence light with the illumination can be used for this purpose.

4. Voxels of Tissue Characteristics

Based on measurements of remitted light intensity and degree of polarization as a function of wavelength and position in measurement space, a three-dimensional model of the tissue comprising an array of individual tissue-characteristic three-dimensional voxels may be produced.

Location and Character of an Anomaly

Without limiting the generality of the inventive concepts or the scope of applications of the disclosures, the embodiments disclosed herein can be basically understood by considering the task of locating, characterizing and distinguishing two different anomalies in tissue, as explained hereafter.

1. Type of Anomaly as a Function of Intensity, Wavelength and Degree of Polarization A schematic representation of a cross section of tissue 1 with two types of anomalies is shown in FIG. 1. One anomaly 2 has lower optical attenuation and the other anomaly 3 has higher optical attenuation, both relative to the surrounding normal tissue 1. Both anomalies are illuminated when the tissue is illuminated by polarized light 4. The light remitted from tissue 1 is filtered to selectively pass different polarizations of light. The filtered polarized light can be detected by a photo-detector such as a photodiode, charge coupled device, or similar light measurement device to obtain a 2D or 3D image data set. The photo-detector may comprise a single point measurement system or may comprise an array of detectors such as an image capture device. A single point measurement system may also optically or mechanically scan to capture an array of measurements. The remitted light intensity is measured by the detector and the intensity information is stored for at least two polarization states. In a preferred embodiment of the invention, the different linear polarizations of the measurement data are captured using cross 5 and parallel 6 of the polarizing filter in the detection path with respect to the orientation of the polarizing filter in the illumination path. These two polarization images are captured using in at least two different wavelengths of illumination light In a preferred embodiment of the invention, multiple wavelengths of illumination are used, for example greater than 30 wavebands. The data captured can form three dimensional data cubes for both parallel and cross polarization states. The data is preferably captured is in the form of an image and the three dimensional data is a hyperspectral image cube containing x and y spatial coordinates as well as the intensity of remitted light from tissue at each wavelength of illumination and for each polarization state. The evaluation of the optical attenuation in the anomalies can be performed by analysis methods incorporating the diffuse reflectance wavelength dependence of the degree of linear polarization parameter $$DLP(\lambda)=(I_P(\lambda)-I_X(\lambda))/(I_P(\lambda)+I_X(\lambda))$$

where $I_P$ and $I_X$ are reflectance intensity at parallel and cross (orthogonal) linear polarization modes, and $\lambda$ is the wavelength of illumination. The anomaly with higher optical attenuation 3 than the surrounding normal tissue experiences less cross polarized signal 5, which leads to the higher degree of polarization value 10 in graph 120. The reflectance intensity from the anomaly with lower optical attenuation 2 provides higher cross polarization detected light intensity 5; therefore, its translation to degree of polarization spectra 110 shows more attenuation 9 compared to surrounding normal tissue DLP spectra 8.

Figure 2:
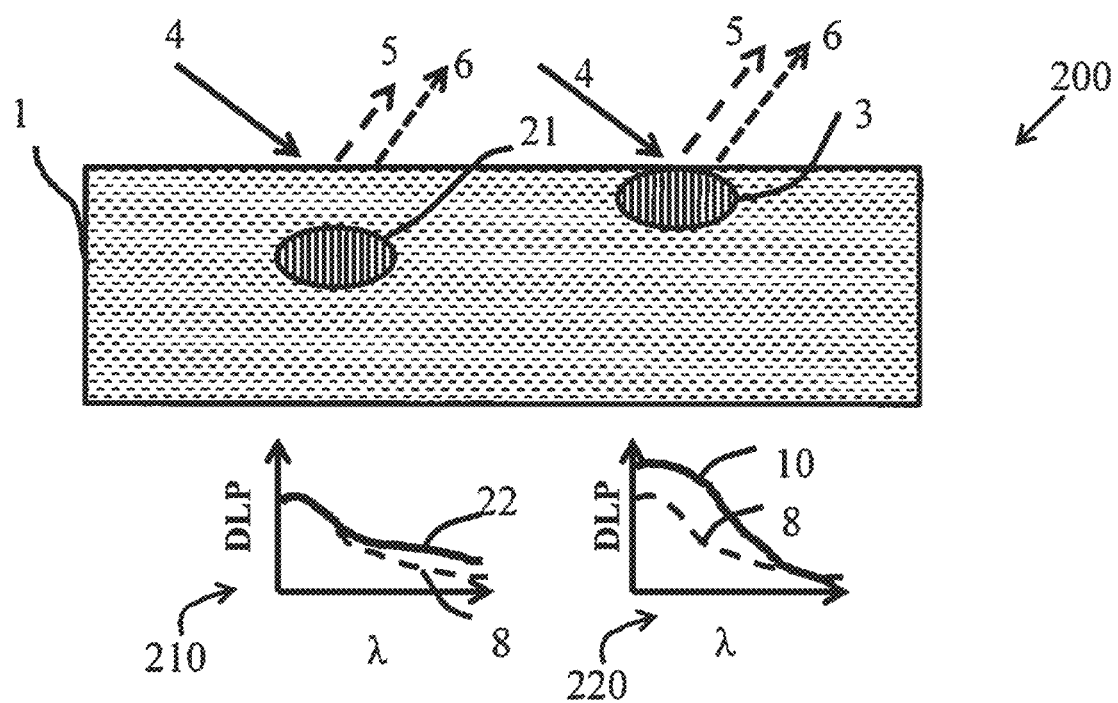
FIG. 2 is a schematic representation of a cross sectional view of biological tissue with two identical anomalies at different depths, and graphs illustrating the corresponding degree of linear polarization spectra variation for the respective anomalies.
Figure 3:
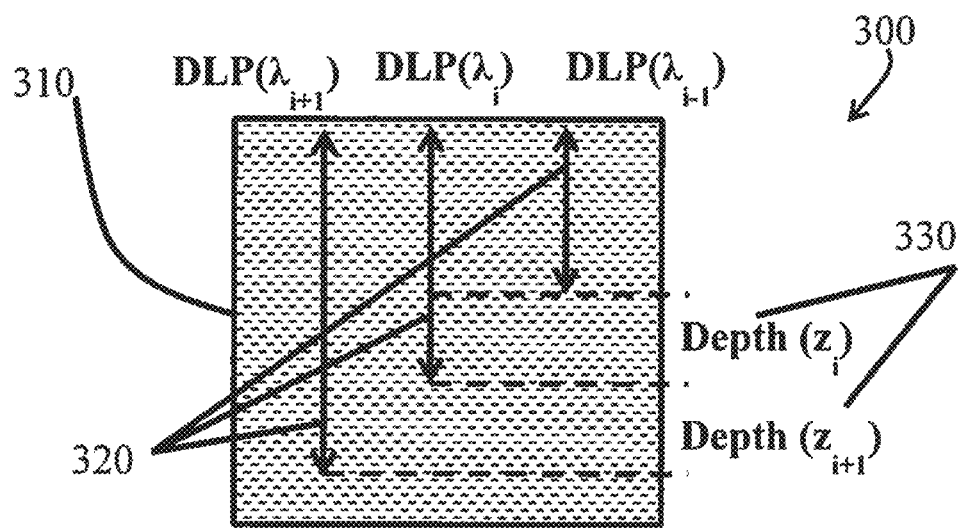
FIG. 3 is a schematic representation of a cross sectional view of a tissue sample showing different depths of illuminating light penetration at different illumination wavelengths.

Referring to FIG. 2, there is shown a schematic representation of a cross section of tissue 1 with two identical anomalies that produce higher optical attenuation relative to the surrounding normal tissue. One the anomalies 21 is deeper beneath the tissue surface. The second anomaly 3 is close to the tissue surface. As in FIG. 1 both anomalies are illuminated by polarized light 4. The light remitted from tissue 1 can be filtered to selectively pass different polarizations of light. The filtered polarized light can be detected by a photo detector such as a photodiode, charge coupled device, or similar light measurement device. The photo-detector may comprise a single point measurement system or may comprise an array of detectors such as an image capture device. A single point measurement system may also optically or mechanically scan to capture an array of measurements. The remitted light intensity is measured by the detector and the intensity information is stored for at least two polarization states. In a preferred embodiment of the invention, the different linear polarizations of the measurement data are captured using parallel 6 and cross 5 orientations of the polarizing filter in the detection path with respect to the orientation of the polarizing filter in the illumination path. These two polarization images are captured in at least two different wavelengths of illumination light.

In a preferred embodiment of the invention, multiple wavelengths of illumination are used, for example greater than 30 wavebands. The data captured can form three dimensional data cubes for both parallel and cross polarization states. The data is captured preferably in the form of an image and the three dimensional data is a hyperspectral image cube containing x and y spatial coordinates as well as the intensity of remitted light from tissue at each wavelength of illumination and for each polarization state. The evaluation of the optical attenuation in the anomalies can be performed by analysis methods incorporating the diffuse reflectance wavelength dependence of degree of linear polarization parameter $$DLP(\lambda)=(I_P(\lambda)-I_X(\lambda))/(I_P(\lambda)+I_X(\lambda))$$

where $I_P$ and $I_X$ are reflectance intensity at parallel and perpendicular (cross) linear polarization modes and $\lambda$ is the wavelength of illumination. The anomaly at greater depth 210 experiences lower cross polarized signal 5 in longer wavelength ranges which leads to the higher degree of polarization value 22 in graph 220.

In further detail, still referring to FIG. 1 and FIG. 2, the DLP spectral signature in 110, 120, 210, and 220 illustrates the power of DLP spectral signature to differentiate the effect of signal changes due to the optical attenuation of an anomaly and the effect of signal changes due to the depth of an anomaly.

2. Depth of Anomaly Related to Intensity, Wavelength and Degree of Polarization

Figure 4:
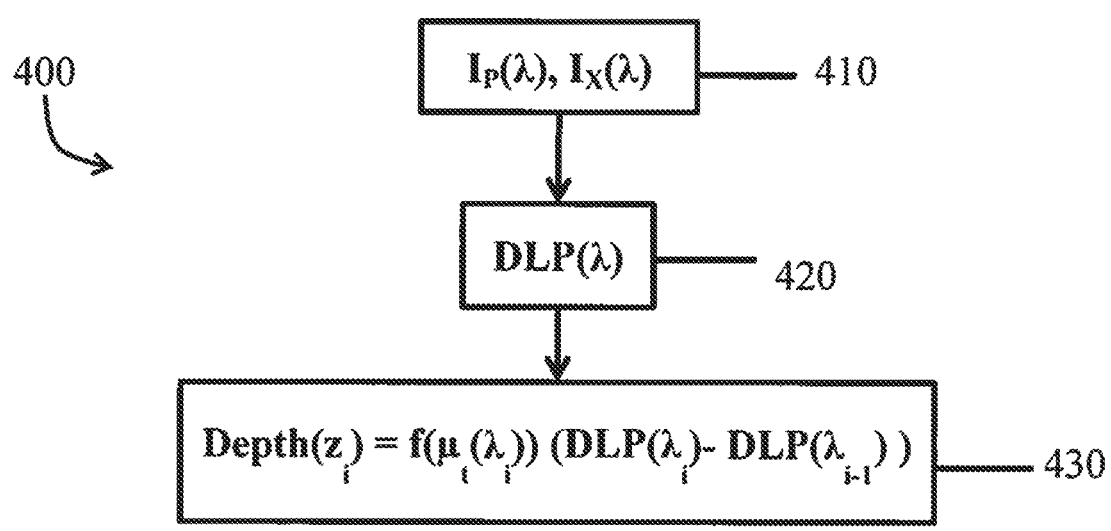
FIG. 4 is a diagramatic representation of a method for extracting depth resolved cross sectional information from two different polarization spectral measurements at each spatial coordinate in the image plane.

Referring now to FIG. 4, the schematic representation of a cross section of a tissue sample 310 illustrate that DLP 320 values calculated from measurements at different wavelengths are representative of tissue characteristics at different depths 330 within the tissue. The longer the wavelengths of illumination, the deeper in the tissue the information comes from. This DLP information can be correlated to the depth within the tissue to create three dimensional maps of tissue optical properties.

Reference is now made to FIG. 4, which shows a flowchart illustrating a preferred method 400 for calculating the depth resolved tissue optical properties (e.g. tissue anomalies 2, 3, 21 in FIG. 1 and FIG. 2). Method 400 comprises first at 410 receiving measurements of intensity at each spatial coordinate from hyperspectral datacubes of tissue sample measurements in both linear polarization modes (i.e. parallel polarized light intensity $I_p(\lambda)$ and cross polarized light intensity $I_x(\lambda)$). Then, at 420, based on those measurements the method features further comprises calculating the degree of linear polarization DLP ($\lambda$). Thus at 430, the method extracts the depth resolved optical absorption or scattering properties of tissue or both, Depth $(Z_i)=f(\mu_t(\lambda_i))$ (DLP $(\lambda_i)$–DLP $(\lambda_i)$) where Z is reflectance as a function of wavelength number and f $(\mu_t(\lambda_i))$ is a correction factor that may be based on an appropriate mathematical model or derived empirically as described in section 2 below.

In another preferred embodiment of the invention, the resulting depth resolved optical properties of tissue 530 can be used to identify the tissue composition (such as melanin, blood concentration) of a skin anomaly or normal tissue in a three dimensional map. This three dimensional map can be used to guide diagnostic or surgical interventions or to monitor the effects of therapeutic interventions.

Dangerous melanomas develop primarily by spreading in depth. The surface spread of the lesion is more easily measured, but not as useful for staging and prognosis as is the Breslow thickness which describes how deeply tumor cells have penetrated into the dermis. The Breslow thickness is prognostic factor in melanoma of the skin, specifically a description of how deeply tumor cells have invaded The task is to identify spectral signature in various wavelength bands including NIR. NIR wavelengths penetrate more deeply because they are less likely to be absorbed/scattered. This provides one way to differentiate between superficial melanin absorption and deeper melanin absorption. When light is scattered as it passes through the tissue it changes its polarization slightly with each scattering event. By comparing the loss of polarization in light remitted from the tissue we have an indication of how deeply that light has penetrated the tissue. The more the polarization has changed from the original polarization, the more deeply the light has penetrated. Both these techniques are used to determine the depth distribution of melanin. Variability in the depth distribution of the melanin across the lesion is a key indicator of melanoma.

Figure 5:
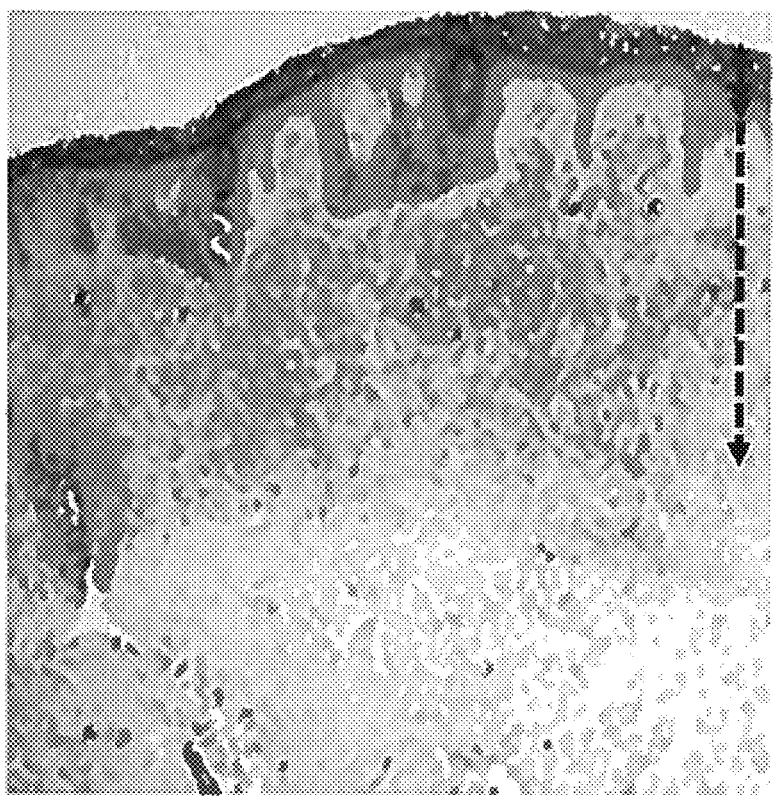
FIG. 5 is a cross sectional image of skin showing melanin in superficial and deep layers of the skin.
Figures 6A, 6B:
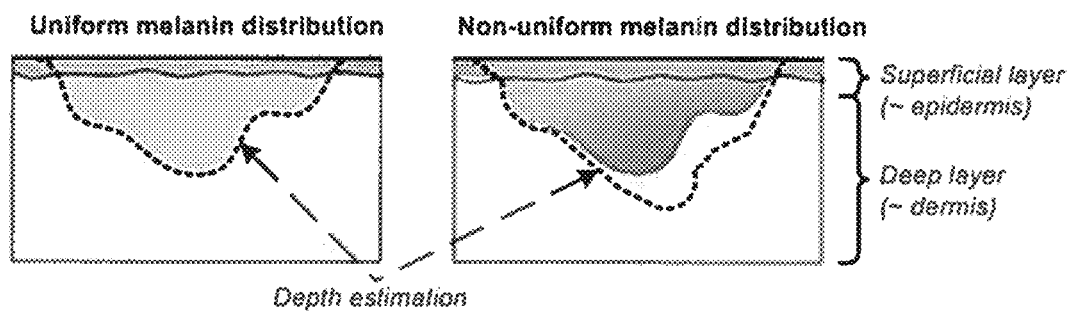
FIG. 6(a) is an illustration of a uniform melanin distribution in skin.
FIG. 6(b) is an illustration of a non-uniform melanin distribution in skin.

As described earlier, by measuring two polarization states of light remitted from skin, the spectral signature of the superficial layer as well as the deep layers of the skin ($A_{POL}$,) can be determined. Spectrally characterizing the superficial layer will yield an estimation of melanin distribution in the superficial layer as shown in FIG. 5 (epidermal layer: 50-120 μm depth). Using this estimation and applying the Beer-Lambert law to compute $f(\mu_t (\lambda_x))$ the depth of the deep melanin at each x-y spatial coordinate can be estimated. Using this approach, non-uniform melanin depth concentration may lead to over or underestimation of depth, but whether the change is due to higher concentration or greater depth (lesion thickness), estimated melanin depth will show as an irregularity in the volumetric analysis FIGS. 6(*a*) and 6(*b*). Similar to examining the border irregularities in the ABCDE approach, volumetric irregularities can be compared as a strong indicator of melanocytic progression or abnormality which is a new capability.

3. Specific Examples

Figure 7:
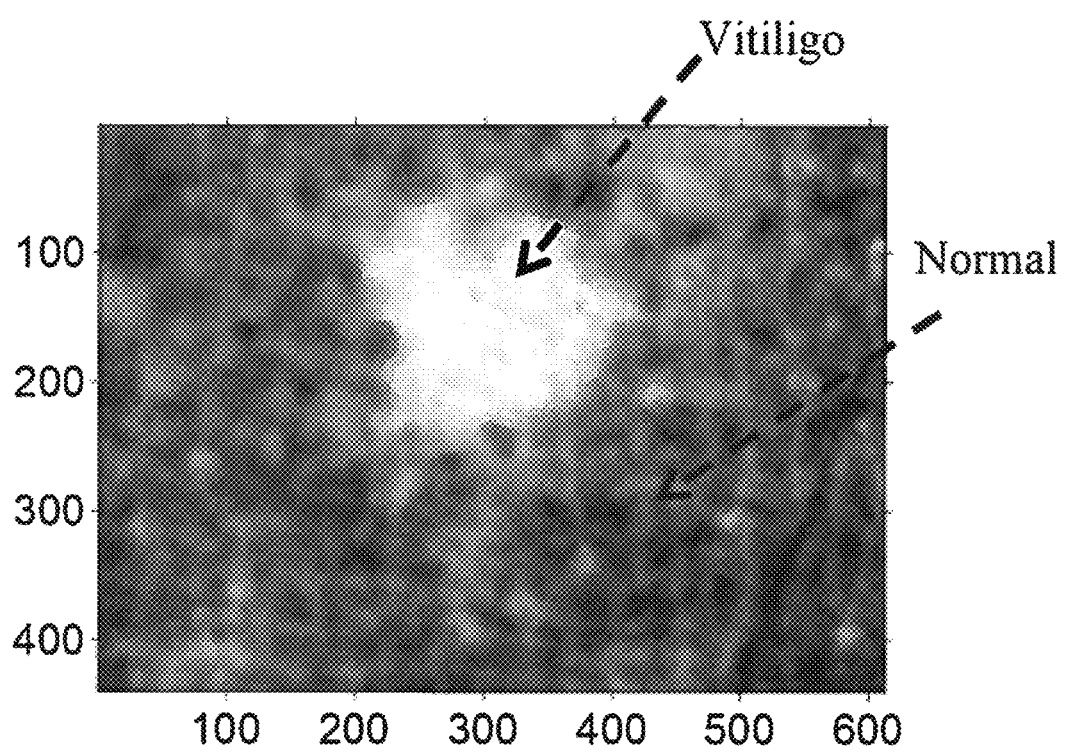
FIG. 7 shows the top view of an example reflectance image of skin exhibiting a feature characteristic of vitiligo.

FIG. 7 shows top view of skin with vitiligo condition as an example of tissue with anomaly. Vitiligo has lower amount of melanin compare to normal skin therefore has lower optical attenuation.

Figure 8:
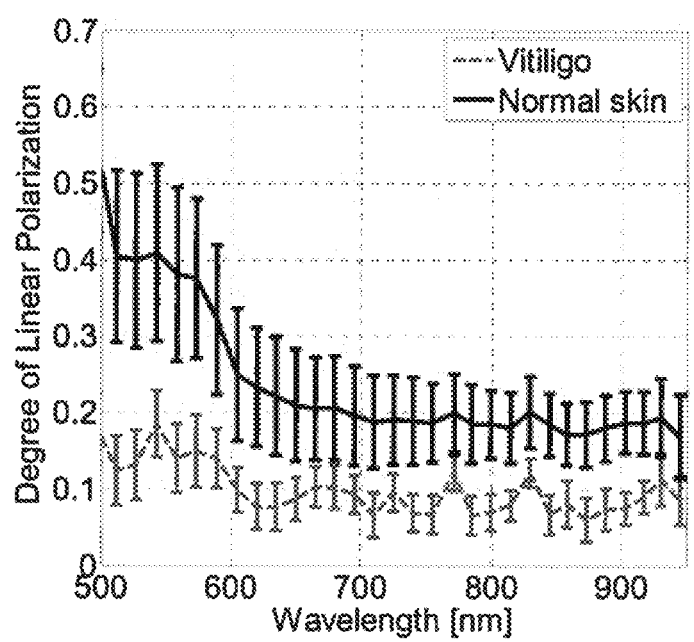
FIG. 8 illustrates the measurements of degree of linear polarization spectra for an example of skin exhibiting a feature characteristic of vitiligo.

FIG. 8 shows the degree of linear polarization for both regions of vitiligo and normal skin condition.

Figure 9:
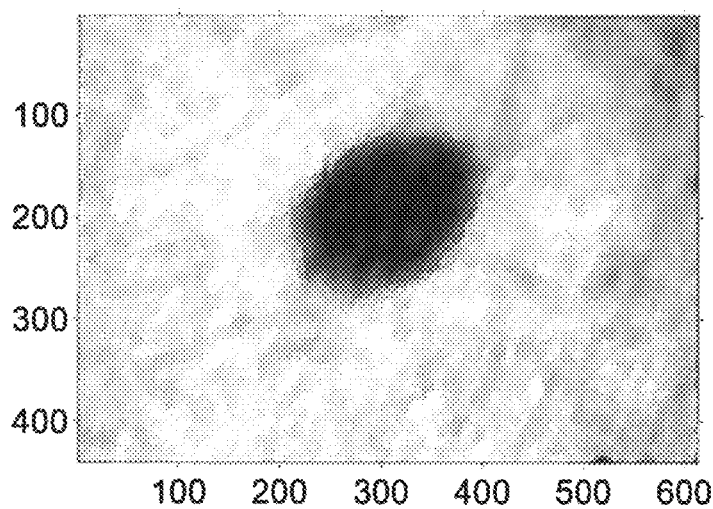
FIG. 9 shows the top view of an example reflectance image of skin exhibiting a feature characteristic of mole condition.

FIG. 9 shows top view of skin with mole condition as an example of tissue with anomaly. Mole has higher quantity of melanin compare to normal skin therefore has higher optical attenuation.

Figure 10:
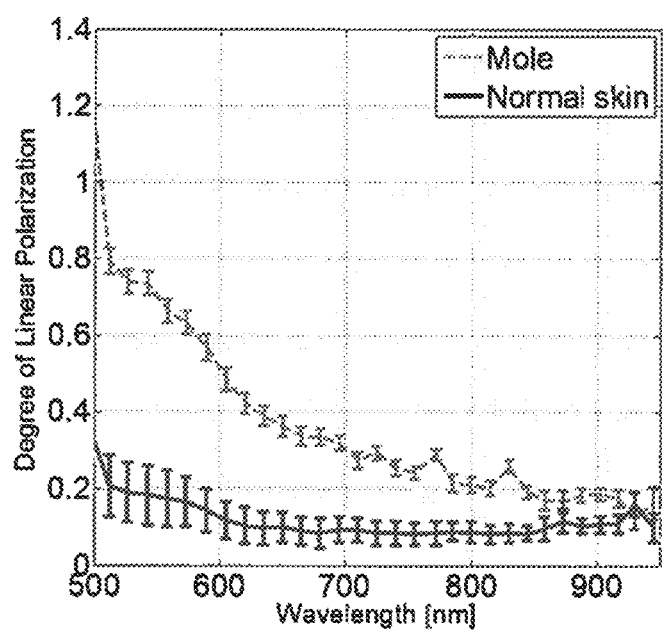
FIG. 10 illustrates the measurements of degree of linear polarization spectra for an example of skin exhibiting a feature characteristic of mole.

FIG. 10 shows the degree of linear polarization for both regions of mole and normal skin condition.

4. Fluorescence Imaging

Referring to FIG. 1, the disclosed technology can provide three dimensional reconstruction of tissue composition using a combination of hyperspectral, fluorescence and polarization based measurements. In this case, an attenuation correction is calculated using a ratio metric analysis of fluorescence anisotropy ("FA") and DLP to correct for attenuation-based artifacts. This calculation takes into account the effect of wavelength difference between excitation and emission wavelengths in DLP measurements by using α and β coefficients derived empirically for a particular tissue type or architecture, and a particular set of excitation and emission wavelengths.

$$\text{Corrected-FA}=FA/(\alpha DLP+\beta)$$

In a preferred embodiment of the invention, method 1100 includes using at least two polarization modes of hyperspectral image cubes 1140 to calculate a three dimensional differential polarization data cube 1160 using the following formula:

$$\Delta POL(\lambda)=I_P(\lambda)-I_X(\lambda)$$

The three dimensional differential polarization data cube 660 is partially dependent on the surface reflection component of parallel polarization described in FIG. 1 and FIG. 2. Reflectance from the surface of the tissue is Lambertian in nature; that the amount of reflectance is proportional to the cosine of the angle of incidence of light encountering the tissue. Flat areas of the tissue appear bright while the areas with ridges and valleys become dark due to angle of incidence between the illuminating light and the tissue. Valleys in the tissue can act as light traps. Therefore, the image derived from the ΔPOL data can transform to a map of tissue surface topography 1170.

Extension to General Tissue Characterization

While the invention has been explained above with reference to the specific example of distinguishing two specific anomalies, it is to be understood that the measurements described herein provide a measurement space of light intensity as a function of position, wavelength and degree of polarization which can be transformed in a three dimensional array of voxels that characterize the tissue. The application of the method and system disclosed herein is not limited to the example described above.

1. Measurement System

Figure 12:
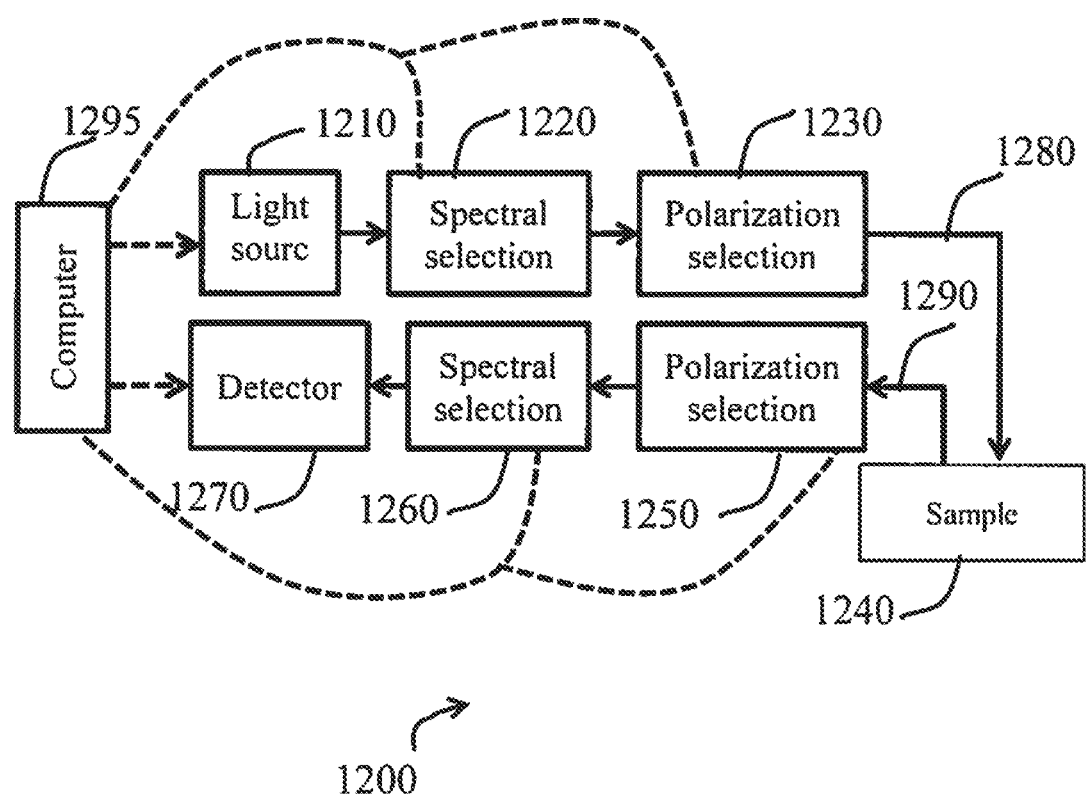
FIG. 12 is a block diagram representation of a system for capturing tissue data using multiple optical modes.

A system for capturing and processing multimode optical measurements is shown in FIG. 12. The system comprises an illumination beam path 1280 which presents illumination light to a sample 1240, an remitted light capture path 1290 that captures and detects light remitted by the sample 1240, and a control and data processing unit 1295 for controlling the illumination and detected light and processing the detected light. The illumination beam path 1280 comprises a light source 1210, an illumination spectral selection unit 1220, and an illumination polarization selection unit 1230. The remitted light capture path comprises an remitted light polarization selection unit 1250, and remitted light spectral selection unit 1260, and a detector 1270. The illumination light source 1210 may be at least one of a broadband lamp, such as tungsten or an arc lamp, a single wavelength laser, a multi-wavelength laser, a super continuum laser, a light emitting diode, or similar sources now or hereafter known in the art. The spectral selection units 1220 and 1260 may be an optical filter, an optical filter wheel, a diffraction grating, a liquid crystal tunable filter, an acousto-optic tunable filter, a plasmonic-based spectral selection device such as a metallic nanostructure, or similar spectral selection devices now or hereafter known in the art. The polarization selection units 1230 may be conventional polarizers such as rotatable crystal or wire grid polarizers or liquid crystal variable retarders, plasmonic metallic nanostructure based filters, or similar devices now or hereafter known in the art. The optical system 1280 may comprise free space optics, such as lenses, mirrors and prisms, fiber optics, integrated optics, liquid light guides, or other technology now or hereafter known in the art that can perform the same function.

In a preferred embodiment, the illumination light source 1210 comprises a Xenon arc lamp incorporated in a spectral programmable light source, such as the product sold under the mark OneLight® Spectra by OneLight Corporation, Vancouver, BC, polarized in only one linear state. The detected light from the tissue sample can be divided into two optical paths comprising cross and parallel polarizations using a beam-splitter and two orthogonally oriented polarizers and each polarization image detected by an individual CCD camera in each path, as will be understood by a person having ordinary skill in the art.

Alternatively, the light remitted from the tissue sample may be spectrally filtered and passed through a polarization selection unit comprising a liquid crystal variable retarder and a linear polarizer that is oriented orthogonally to the illumination polarization. The liquid crystal variable retarder can be controlled to selectively rotate the polarization of the light remitted from the tissue sample prior to passing it through the linear polarizer, such that the fixed linear polarizer can act as a cross, 45 degree, parallel, or any other angle of polarization filter and the signal from each state can be sequentially captured with a single CCD camera.

In another embodiment of the invention, the system for acquiring the information may be deployed in an endoscopic measurement by delivering hyperspectral, polarized light though a light pipe or optical fiber, and receiving remitted light through the same or a separate light pipe or optical fiber. Applicable polarization selection and spectral filtering methods may be selected by a person having ordinary skill in the art.

2. Characterizing Tissue by Solving a Multi-Dimensional Inverse Problem

Figure 11:
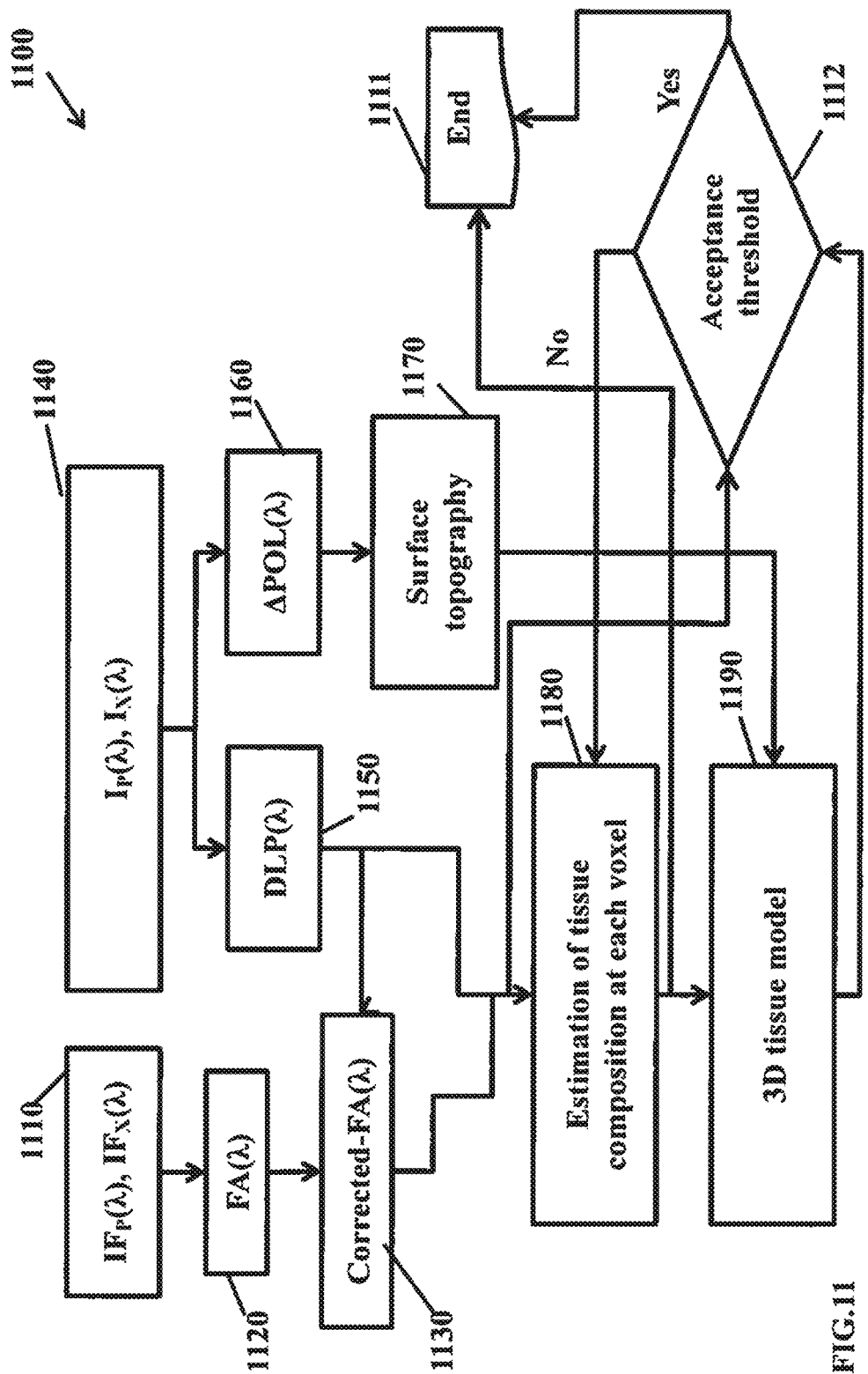
FIG. 11 is a diagramatic representation of a method for creating a three dimensional map of tissue composition using hyperspectral data in different polarization modes.

The general goal of this disclosure is to arrive at an accurate three-dimensional representation of the structural characteristics of the tissue being tested based on multimode optical measurements. To obtain an accurate, high resolution model in a reasonable period of time, the disclosed system starts with the multimode measurements, produces values for the degree of linear polarization and fluorescence anisotropy as functions of wavelength $\lambda$. and position x',y' in measurement space, and estimates the structural characteristics of the tissue. Thereafter, the system corrects those characteristics based on comparisons of the predicted effect of the estimated structural characteristics on measured values or the linear polarization and fluorescence anisotropy. This is done by solving a multi-dimensional inverse problem as generally shown in FIG. 11.

An estimation module 1180 produces tissue structural characteristics based on multi-mode optical measurements of tissue; that is, the principal inputs to the estimation module are the degree of linear polarization as a function of wavelength and location of a detector element in measurement space, DLPx',y'($\lambda$), and the corrected fluorescent anisotropy as a function of wavelength and location of a detector element, FAx',y'($\lambda$), in measurement space, and produces as its output the structural characteristics of the tissue, such as the amount and location melanin in the tissue. Initially, the parameters of that model are estimated based on knowledge of the likely response of normal tissue to the illumination light that is to be used in the test and, if available, some understanding of the changes that might be caused by pathologies that may be present in the tissue. Those estimates are implemented by setting initial conditions for parameters of the estimation module.

A three-dimensional forward model 1190 is provided that predicts the optical response of tissue that should occur based on tissue structural characteristics, e.g., the amount and location of melanin in the tissue, and knowledge of the incident illumination light to be applied in the test, Ix,y($\lambda$) 1140; that is, the principal inputs of the forward model are structural characteristics of the tissue, and the principal outputs are the expected DLPx',y'($\lambda$) 1150 and FAx',y'($\lambda$) 1130. Another input to the forward model 1190 is data representing the surface topography of the tissue produced by module 1170 in response to differences in the degree of linear polarization as a function of wavelength and the location of a detector element in measurement space, $\Delta$DLPx',y'($\lambda$), computed by module 1160. The tissue structural characteristics produced by the estimation module 1180 are provided as inputs to the forward model to produce as an output from the forward model the expected DLPx',y'($\lambda$) 1150 and FAx',y'($\lambda$) 1130 based on the known illumination light, the parameters of the inverse model and $\Delta$DLPx',y'($\lambda$) 1160.

The DLPx',y'($\lambda$) 1150 and FAx',y'($\lambda$) 1130 outputs produced by the forward model are then compared to the actual DLPx',y'Q($\lambda$) and FAx',y'($\lambda$) produced by measurements. The differences, if any within the acceptance tolerance, are used to alter the parameters of the estimation module 1180 and new tissue structural characteristics are applied to the input of the forward model 1190, and so forth, until all the outputs DLPx',y'($\lambda$) 1150 and FAx',y'($\lambda$) 1130 from the forward model 1190 are within acceptance thresholds at unit 1112. At that point, the output of the system comprises the final structural tissue characteristics produced by the estimation module 1180. Thus, an inverse model algorithm implement by the foregoing modules and forward model will be applied to determine the tissue composition at each voxel.

The forward model 1190 of the system may use various models for the propagation of light through tissue, such as the Monte Carlo method, diffusion theory, the random walk method, a radiative transfer model, or other similar models known in the art.

Among the properties that may be taken into account are tissue composition and optical properties including the known absorption, scattering and fluorescence properties of tissue. The output of any of the forward models is a data set corresponding to the data measured by measurement system 1200. The inverse problem algorithm postulates an initial state based on the standard or ideal forward model tissue composition values. It also postulates limits to the relative contribution of the tissue composition inputs that correspond to the real biological limits of the tissue composition. The inverse problem algorithm then iteratively adjusts the relative amounts of the tissue composition characteristics of the forward model until the output dataset and the measurement dataset converge. The limits to the relative tissue composition inputs constrain the iterations to stay within the bounds of biological plausibility and limit unnecessary calculations allowing the algorithm to converge faster and more efficiently.

3. Simplified Hyperspectral and Polarization System

Figure 13:
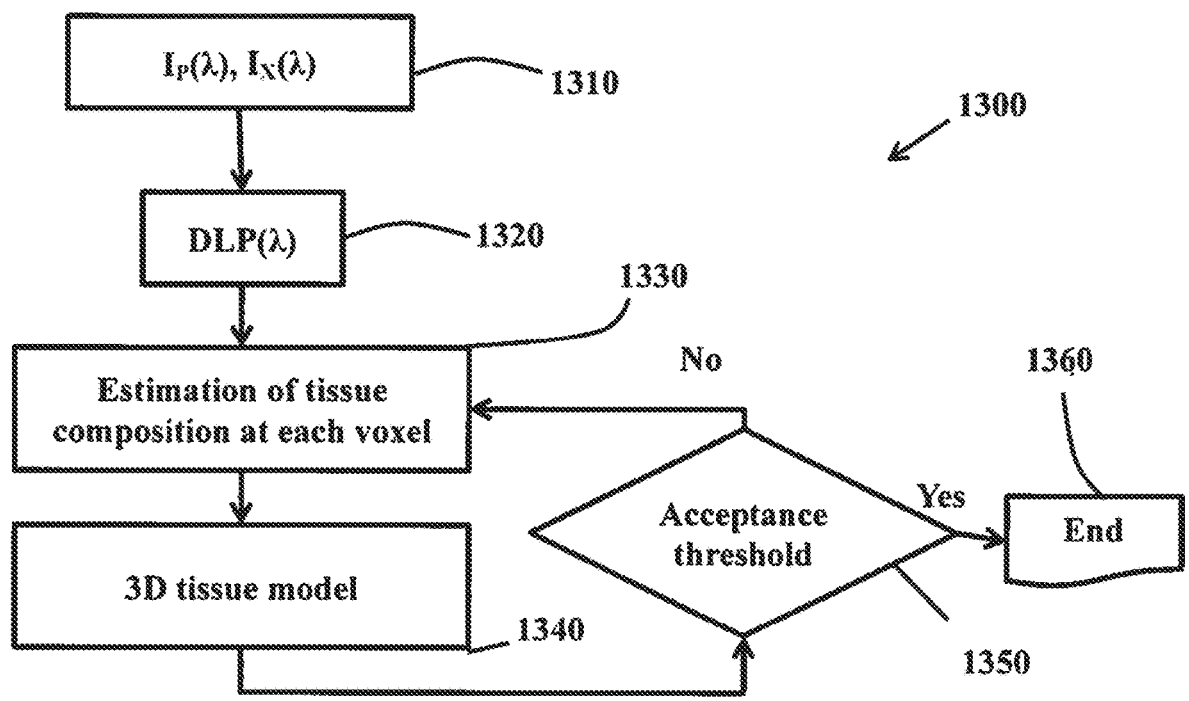
FIG. 13 is a diagramatic representation of a method for creating a three dimensional map of tissue composition using fluorescence and hyperspectral data in different polarization modes.

FIG. 13 illustrates a simplified system 1300 of three-dimensional tissue characterizations using only hyperspectral and polarization based measurements. This includes using at least two polarization modes of hyperspectral data 1310 to create a degree of linear polarization spectral signature 1320. Exemplary polarization modes include linear polarized illumination and linear polarized detection in parallel, 45 degree, crossed or other orientations. The system 1300 may include the DLP spectral signature 1320 can be used to extract the initial estimate for three dimensional optical property of targeted tissue 1330. The three dimensional optical property of targeted tissue comprises at least two layers. The method 1300 may further include extracting the estimate of three dimensional composition and anatomical tissue mapping which can be used in three dimensional tissue models 1340.

System 1300 solves an inverse problem in the same way as described with respect to system 1100, and may use any of the forward models described above.

4. Simplified Hyperspectral, Fluorescence and Polarization System

Figure 14:
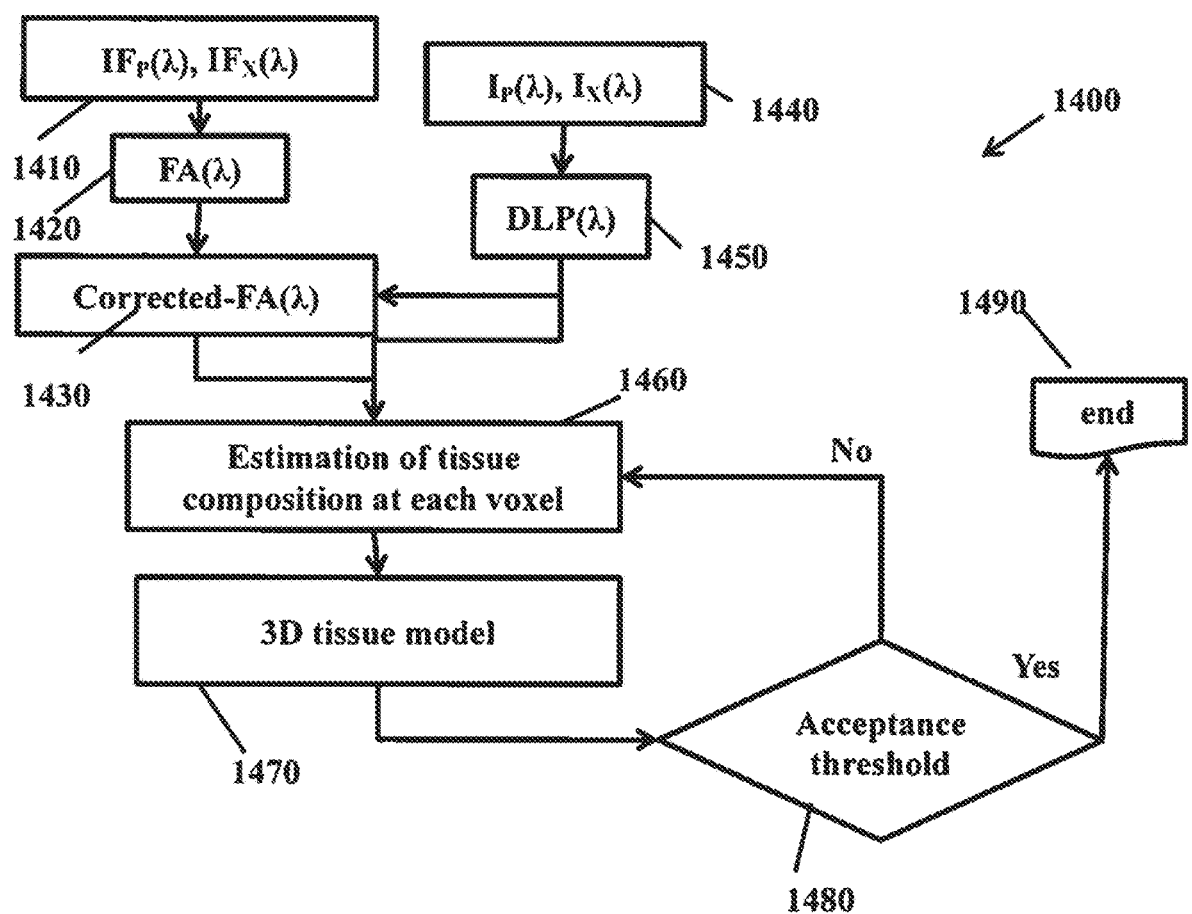
FIG. 14 is a diagramatic representation of a method for creating a three dimensional map of tissue composition using tissue surface topography and fluorescence and hyperspectral data in different polarization modes.

FIG. 14 illustrates a simplified system 1400 of three dimensional reconstruction of tissue composition using hyperspectral, fluorescence and polarization based measurements. This simplified system includes using at least two polarization modes of hyperspectral data 1440 to create a degree of linear polarization spectral signature 1450. Exemplary polarization modes include linear polarized illumination and linear polarized detection (relative to excitation) in parallel, 45 degree, perpendicular and other orientations.

System 1400 may further include hyperspectral data in the form of hyperspectral image data. The hyperspectral image data may be structured in the form of a hyperspectral data cube comprising at least two polarization modes of fluorescence images 1410.

The two polarization modes of fluorescence images 1410 can be analyzed to create fluorescence anisotropy mapping 1420. The method 1400 may further include attenuation correction of fluorescence anisotropy 1430 map using DLP mapping 1450 at the same wavelength range of corresponding fluorescence emission wavelength.

System 1400 may include the DLP spectral signature 1450, and corrected fluorescence mapping 1430 can be used to extract the initial estimate for three dimensional optical property of targeted tissue 1460, down to the level of molecular signatures (of tissue components that have characteristic fluorescence). The three dimensional optical property of targeted tissue comprises at least two layers. The method 1400 may further include extracting the estimate of three-dimensional composition and anatomical tissue mapping which can be used in three dimensional tissue models 1470.

System 1400 solves an inverse problem in the same way as described with respect to system 1100, and may use any of the forward models described above.

Elimination of Melanin Masking

Embodiments of a method and subsystem for essentially eliminating the masking effect of superficial melanin and scattering are also disclosed herein. The method and system provide a polarized attenuation function $A_{POL}$ for more accurate skin chromophore quantification than prior multi-wavelength imaging techniques which, as discussed above, produce unlikely correlations between melanin and hemoglobin in their chromophore maps or implausible oxygen saturation for skin with high melanin content.

The method uses in vivo, non-invasive, hyperspectral, polarization sensitive imaging of skin based on spectrally reflected and back-scattered light to determine anatomical and functional characteristics of skin with melanin or hemoglobin variations. The apparatus produces, and the method employs, two orthogonal, linear polarized hyperspectral image intensity datacubes. The method yields biologically plausible chromophore maps when applied to highly pigmented regions of skin.

1. In Vivo, Non-Invasive, Polarized Hyperspectral Data Capture

A dermoscope that enables in vivo, non-invasive polarized hyperspectral imaging of skin is provided, comprising a hyperspectral light source, polarization and other optics for illuminating a target and collecting remitted light, image detectors and control analysis software that enables the multimode imaging-based measurement of skin lesions.

Figure 15:
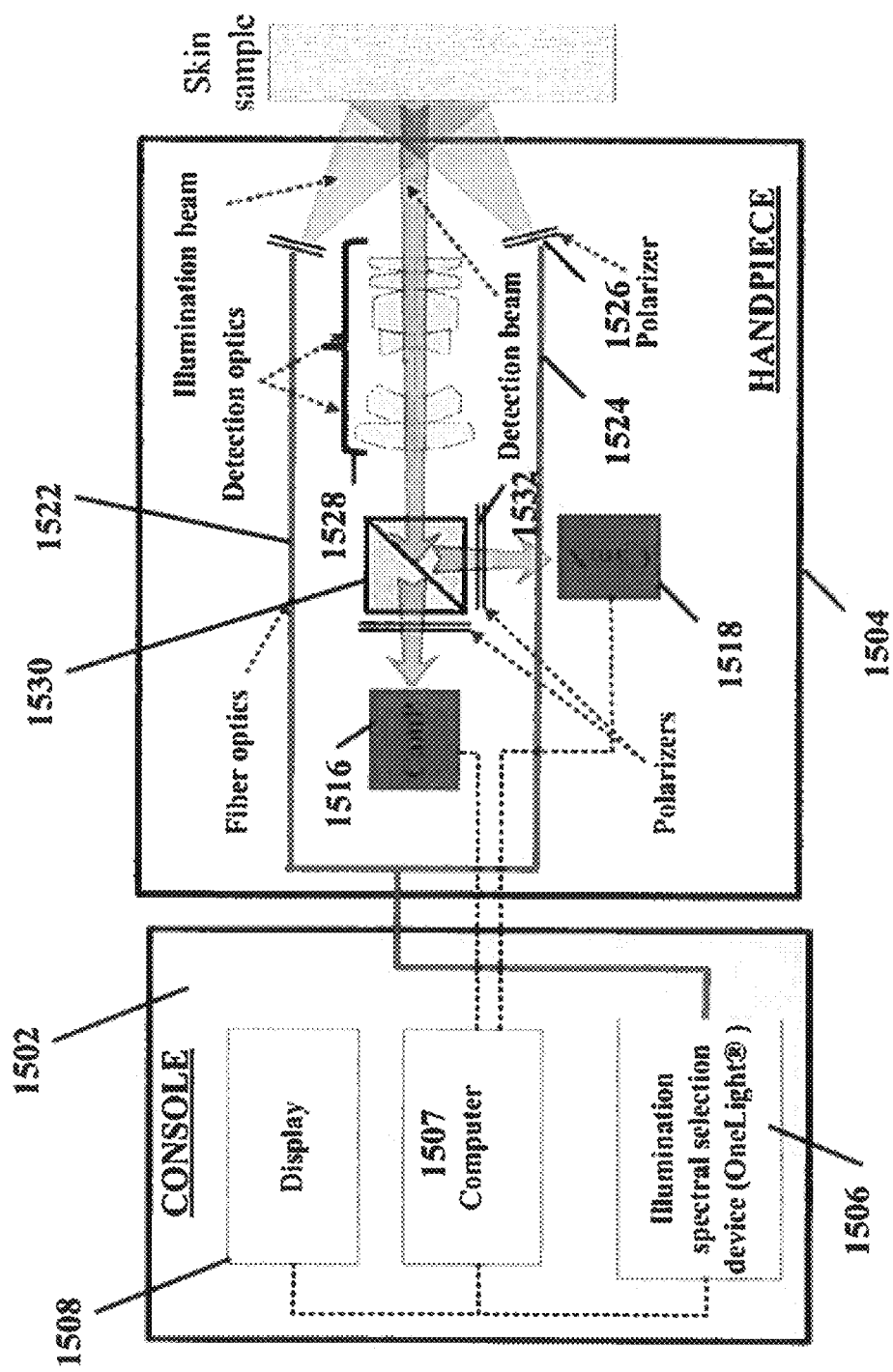
FIG. 15 is a block diagram of a first embodiment of a system for implementing hyperspectral, polarization distinguishing optical measurements as described herein.

As shown in FIG. 15, a first embodiment of the dermoscope that enables in vivo, non-invasive, polarized hyperspectral imaging of skin broadly comprises a console 1502 and a handpiece probe 1504. A computer in the console provides and controls the specimen illumination and data acquisition, image processing, archiving and data transmission. In a specific example, the illumination light is produced by a spectrally programmable OneLight® Spectra illumination system 1506 having a Xenon arc light source and microelectromechanically-based wavelength selection ability over the range from 468 nm to 857 nm. However, it is to be understood that other broad spectrum light sources and other spectral selection devices could be used without departing from the principles of the invention. The console further comprises a computer 1507 and a display 1508 as well as appropriate input and output and data storage devices. The handpiece 1504 comprises two cameras; a beam splitter 1520; and fiber guides 1522 and 1524 that direct the light from the console illumination source to a fixture that positions this assembly at the correct depth to illuminate the tissue surface. The device preferably provides diffuse illumination to skin in a geometry that limits the amount of specular reflection to the detector. A ring-shaped linear polarizer 1526 is placed in front of the fiber optics to allow only linearly polarized light to illuminate the tissue surface. The two cameras share multi-element imaging optics 1528 and each camera has a polarization filter 1530 and 1532 respectively, which are oriented orthogonally to one another. This configuration captures images of the skin that maintain the linear polarization present in reflectance from both surface and deeper layers of tissue, and cross polarization images. Synchronized image acquisition by the two spatially registered cameras generates two images of an 11 mm×16 mm area of skin in both parallel and cross polarizations.

Figure 16:
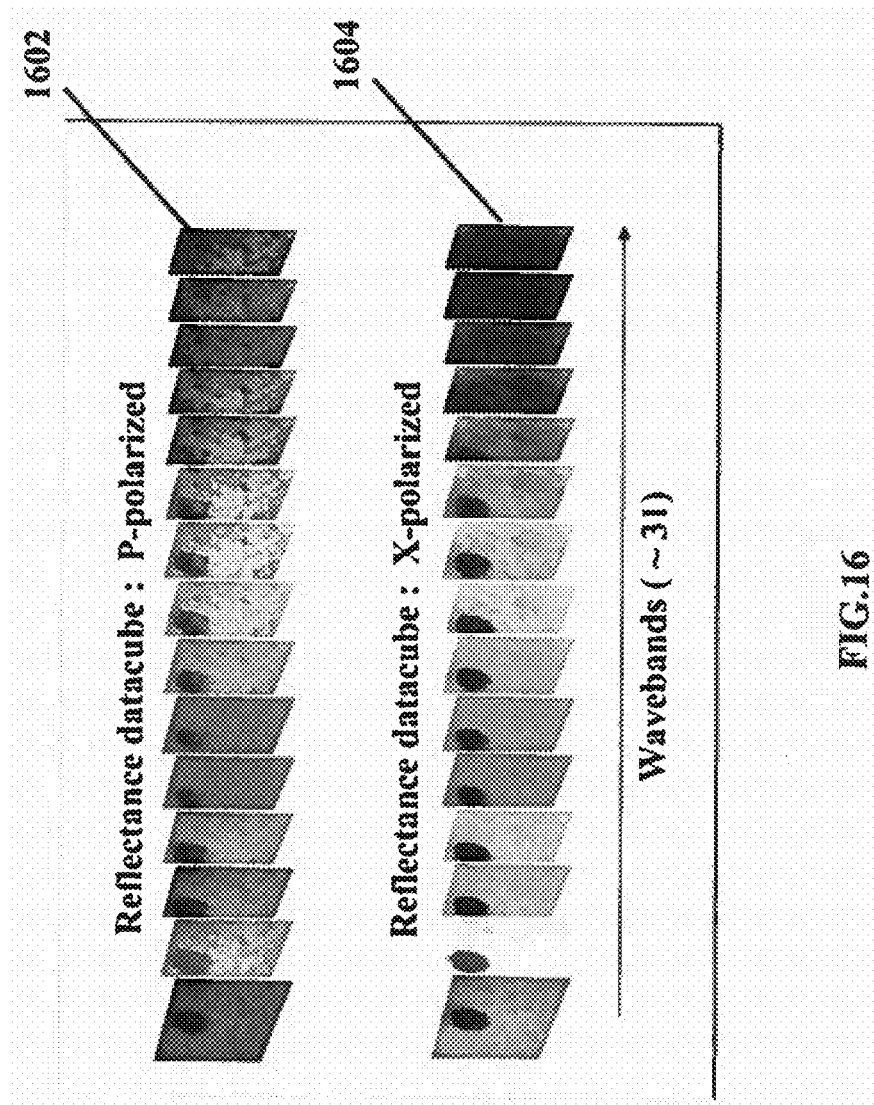
FIG. 16 is an illustration of hyperspectral datacubes produced by the system of FIG. 15.

As shown in FIG. 16; parallel polarized image stacks 1602 and cross polarized image stacks 1604 are acquired by hyperspectral imaging of the target area enabled by the sequential illumination with 33 wavelength bands from visible (468 nm) to near infrared range (857 nm), with a wavelength step interval of ~13 nm. Typical spectral scan ranges are from 450 to 950 nm, and comprise 30-50 wavelengths. Digital color images can be generated by programming the light source for broadband illumination to mimic typical Bayer filters that are used in conventional color cameras, or by image processing. These color images are provided for display or for comparison with standard dermoscopes. Additional system details for a specific such device are described in MacKinnon, N. B., et al. In vivo skin chromophore mapping using a multimode imaging dermoscope (SkinSpec™), *Proc. SPIE,* 8587, 85870U (2013). In FIG. 16, the minimum spatially resolvable line-width detected by the P and X cameras was approximately 110 man, measured by imaging a USAF 1951 resolution test target.

Figure 22:
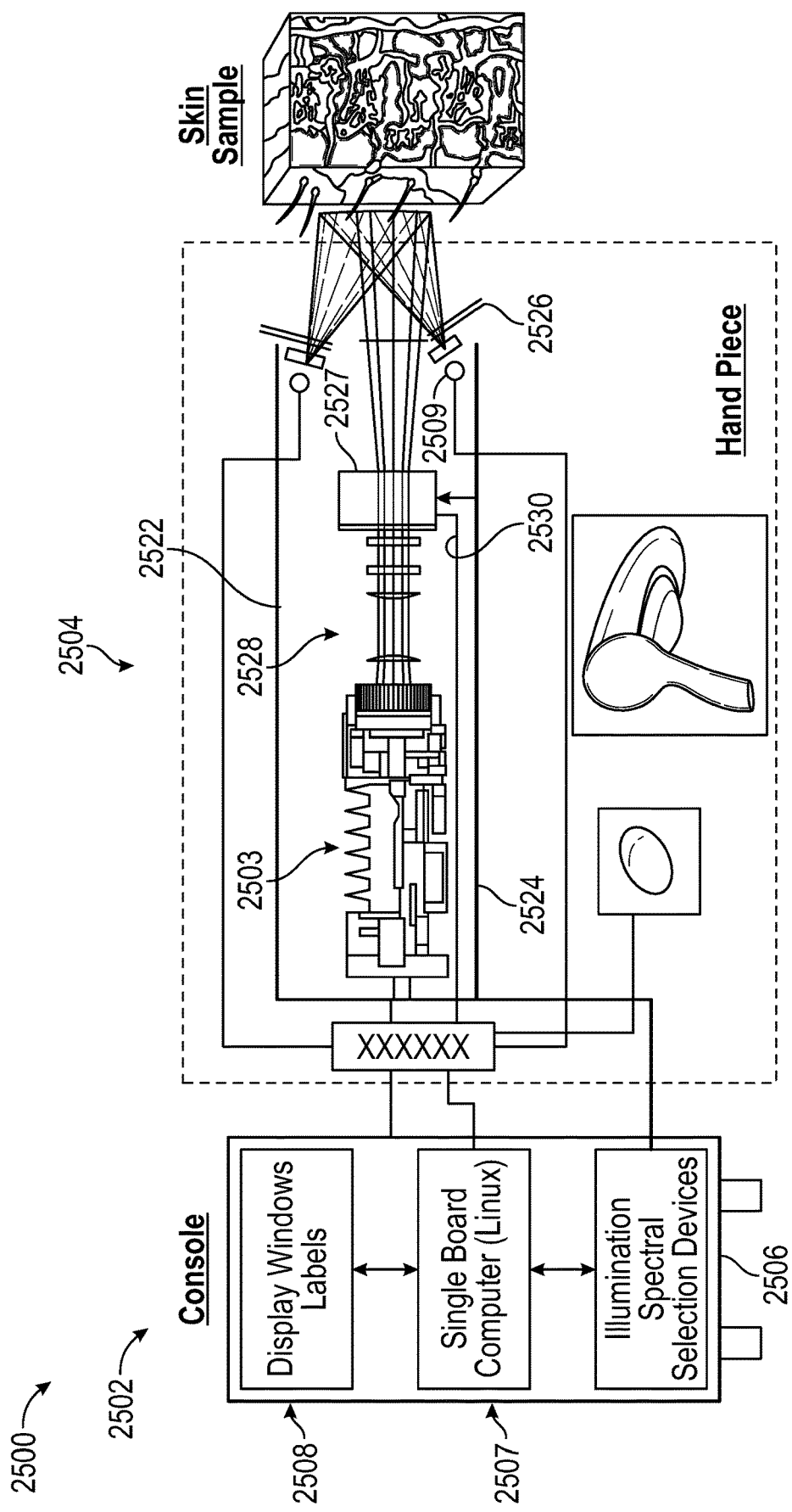
FIG. 22 is a block diagram of a second embodiment of a system for implementing hyperspectral, polarization distinguishing optical measurements as described herein.

FIG. 22 shows a second embodiment 2500 of the dermoscope which broadly comprises a console 2502 and a handpiece probe 2504. A computer in the console provides and controls the specimen illumination and data acquisition, image processing, archiving and data transmission. In a specific example, the illumination light is produced by a spectrally programmable illumination system 2506 having, preferably, a Xenon arc light source and microelectromechanically-based wavelength selection ability over the range from 450 nm to 950 nm.

In addition, one or more light emitting diodes (LEDs) 2509 are provided, preferably in the handpiece probe, to produce high power illumination light at one or more specific wavelengths (e.g., blue) which excites fluorescence by the skin. Depending on the choice of excitation and detection wavelengths, different chemical components in the skin (both intrinsic and externally added) can be thus imaged and characterized, by their fluorescence intensity. The console further comprises a computer 2507 and a display 2508 as well as appropriate input and output and data storage devices. The handpiece 2504 further comprises a camera 2503; and fiber guides 2522 and 2524 that direct the broad spectrum light from the console illumination source to a fixture that positions this assembly at the correct depth to illuminate the tissue surface. The handpiece preferably provides diffuse illumination to skin in a geometry that limits the amount of specular reflection to the detector. A ring-shaped linear polarizer 2526 is placed in front of the fiber optics and the LEDs to allow only linearly polarized light to illuminate the tissue surface.

In this embodiment, a variable retarder, preferably a liquid crystal variable retarder (LVCR) 2527 that covers the targeted spectral range, is provided to select the polarization of light to be imaged. This can be achieved dynamically, with the LCVR (2527) changing polarization under control from computer 2507. The camera employs multi-element imaging optics 2528.

Figure 23:
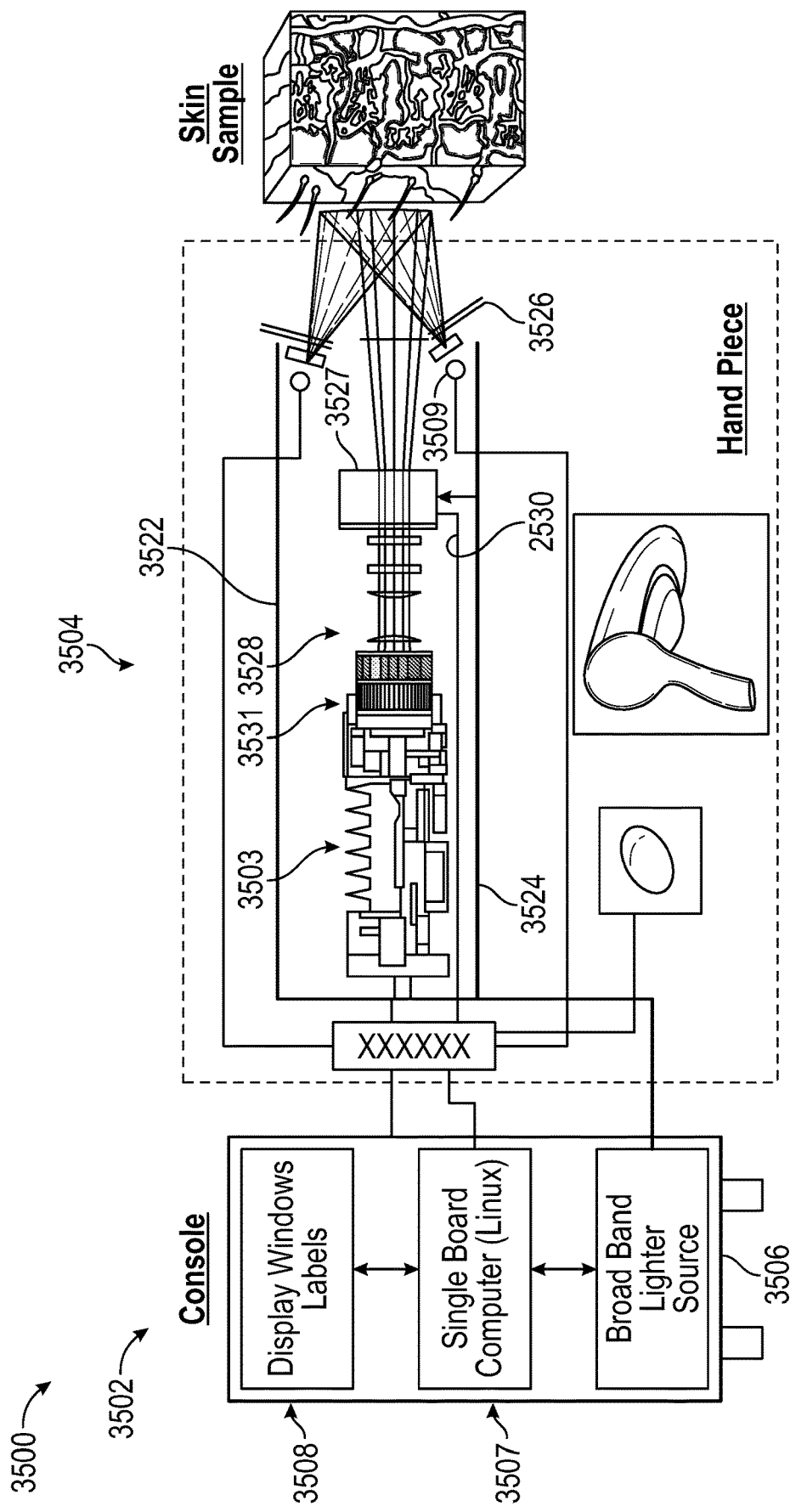
FIG. 23 is a block diagram of a third embodiment of a system for implementing hyperspectral, polarization distinguishing optical measurements as described herein.

FIG. 23 shows a third embodiment 3500 of the dermoscope which broadly comprises a console 3502 and a handpiece probe 3504. A computer in the console provides and controls the specimen illumination and data acquisition, image processing, archiving and data transmission. In a specific example, illumination light is produced by a broad band (white light) illumination system 3506 that preferably produces light over a wavelength range of at least 450 nm to 950 nm. This could be, for example, a Xenon arc light source. Also, one or more light emitting diodes (LEDs) 3509 are provided, preferably in the handpiece probe, to produce high power illumination light at one or more specific wavelengths (e.g., blue) which excites fluorescence by the skin. The console further comprises a computer 3507 and a display 3508 as well as appropriate input and output and data storage devices. The handpiece 3504 further comprises a camera 3503; and fiber guides 3522 and 3524 that direct the broad spectrum light from the console illumination source to a fixture that positions this assembly at the correct depth to illuminate the tissue surface. The handpiece preferably provides diffuse illumination to skin in a geometry that limits the amount of specular reflection to the detector. A ring-shaped linear polarizer 3526 is placed in front of the fiber optics and the LEDs to allow only linearly polarized light to illuminate the tissue surface.

In this embodiment, a variable retarder, preferably a liquid crystal variable retarder (LVCR) 3527, is provided together with a single polarization filter 3530 to select the polarization of light to be imaged, as described above with respect to FIG. 22. The camera employs multi-element imaging optics 3528. In addition, this embodiment includes a spectral selection device 3531 to select the wavelength being imaged so as to enable hyperspectral imaging by filtering the light remitted from the tissue, rather than illuminating the tissue with selected wavelengths.

2. Computed Optical Spectra Density, $OD_\perp$ and Polarized Attenuation Spectrum, $A_{POL}$ A calibration step is required to adjust the spatial and spectral intensity $Z(x, y, \lambda)$, responses of the instrument, to correct for detector response, light source characteristics, and the instrument transfer functions. The imaging software determines camera exposure times for individual wavebands to optimize the cameras' dynamic range independent of illumination intensity variations. The calibration datacubes from imaging a Spectralon™ reflectance surface in both parallel ($Z_\parallel$) and perpendicular ($Z_\perp$) polarization states are computed using the following equations:

$$Z_\parallel(x, y, \lambda) = \frac{R_{\parallel skin}(x, y, \lambda)}{R_{\parallel spectralon}(x, y, \lambda)}, \text{ and} \quad (1)$$

$$Z_\perp(x, y, \lambda) = \frac{R_{\perp skin}(x, y, \lambda)}{R_{\perp spectralon}(x, y, \lambda)}$$

where $R_{\parallel skin}$ and $R_{\perp skin}$ are the reflectance measurements of skin hyperspectral images by parallel and cross polarized cameras. $R_{\parallel spectralon}$ and $R_{\perp spectralon}$ are the reflectance measurements of Spectralon hyperspectral images by the same parallel and cross-polarized cameras. Because Spectralon and skin scatter light differently, this portion of the calibration process may introduce a small error, requiring a "calibration factor" ($f_{x,y,\lambda}$), as discussed in Jacques, S. L., McAuliffe, D. J. The melanosome: threshold temperature for explosive vaporization and internal absorption coefficient during pulsed laser irradiation. *Photochem. Photobiol*, 53, 769-775 (1991). Unlike in the use of DLP, as described above, this calibration factor may be ignored as it cancels out, as shown in the following equations.

Both $Z_\parallel$ and $Z_\perp$ are affected by the superficial melanin absorption ($T_{mel\_x,y,\lambda}$) acting as an absorption filter on the skin surface. To remove the effect of superficial melanin attenuation on the spectrum of deeper skin chromophores, a polarization attenuation function, $\Delta_{POL}$ is introduced:

$$A_{POL} = \log\left(\frac{Z_\parallel - Z_\perp}{Z_\parallel}\right) = \quad (2)$$

$$\log\left(\frac{Z_{Superficial}}{Z_\parallel}\right) = \log\left(\frac{T_{mel\_x,y,\lambda} \cdot G_{x,y,\lambda} \cdot f_{x,y,\lambda} \cdot R_{Superficial}}{T_{mel x,y,\lambda} \cdot G_{x,y,\lambda} \cdot f_{x,y,\lambda} \cdot R_\parallel}\right) \text{ and}$$

$$A_{POL} = \log(R_{Superficial}) - \log(R_\parallel) \quad (3)$$

where $Z_{Superficial}$ is the reflectance of the skin superficial layer obtained by subtraction of the cross polarization image cube from the parallel polarization image cube. Jacques, S. L., Ramella-Roman, J. C., & Lee, K. Imaging skin pathology with polarized light, *J Biomed Opt*, 7, 329-340 (2002) Morgan, S. P. & Stockford, I. M. Surface-reflection elimination in polarization imaging of superficial tissue, *Opt. Lett.*, 28, 114-116 (2003). Arimoto, H. Multispectral Polarization Imaging for Observing Blood Oxygen Saturation in Skin Tissue., *Appl Spectrosc*, 60, 459-464 (2006). Equation (2) shows how the calibration factor ($f_{x,y,\lambda}$) and scattering function ($G_{x,y,\lambda}$) at each pixel (x,y) and wavelength ($\lambda$) can be corrected by the division of $Z_{Superficial}$ by $Z_\parallel$. $R_{Superficial}$ is the backscatter light mainly from the pigmented epidermis. $Z_\parallel$ includes superficially and deeply penetrating reflected light affected by both superficial and deep melanin as well as oxy- and deoxy-hemoglobin. Conventionally the optical density function OD has a minus sign in the logarithmic function, $OD_\perp = -\log(Z_\perp(x, y, \lambda))$. However in the $A_{POL}$ logarithmic function, $Z_\parallel$ is in the denominator, the minus sign is not required. Both $Z_\parallel$ and $Z_{Superficial}$ include surface glare. By introducing the $A_{POL}$ function, by division of $Z_\parallel$ and $Z_{Superficial}$ the surface glare signal which may affect absorber quantification will be substantially canceled out.

The natural logarithm of $R_{Superficial}$ and $R_\parallel$ can be linearly correlated with chromophore concentration using the Beer-Lambert Eq. as shown in Eq. 4 and Eq. 5 as follows:

$$\log(R_{Superficial}(x,y,\lambda)) = -(\varepsilon_m(\lambda) \cdot C_{m-s}(x,y) \cdot L_{m-s}(x,y,\lambda)) \quad (4)$$

$$\log(R_\parallel(x,y,\lambda)) = -((\varepsilon_m(\lambda) \cdot C_{m-s}(x,y) \cdot L_{m-s}(x,y,\lambda)) + (\varepsilon_m(\lambda) \cdot C_{m-d}(x,y) \cdot L_{m-d}(x,y,\lambda)) + (\varepsilon_{Hb}(\lambda) \cdot C_{Hb}(x,y) \cdot L_{Hb}(x,y,\lambda)) + (\varepsilon_{oHb}(\lambda) \cdot C_{oHb}(x,y) \cdot L_{oHb}(x,y,\lambda))) \quad (5)$$

where $C_{m-s}$, $C_{m-d}$, $C_{Hb}$, and $C_{oHb}$ are the relative concentration of superficial and deep melanin, deoxy- and oxy hemoglobin, respectively; $\varepsilon_m$, $\varepsilon_{Hb}$, $\varepsilon_{oHb}$ are the absorption coefficients for melanin, deoxy-hemoglobin, and oxy-hemoglobin, respectively; $L_{m-s}$, $L_{m-d}$, $L_{Hb}$, and $L_{oHb}$ are the optical pathlength of superficial and deep melanin, deoxy- and oxy hemoglobin, respectively.

By substituting Eq. 4 and Eq. 5 into the Eq. 3, the polarization attenuation datacube is found as follows:

$$A_{POL}(x,y,\lambda) = (\varepsilon_m(\lambda) \cdot C_{m-d}(x,y) \cdot L_{m-d}(x,y,\lambda)) + (\varepsilon_{Hb}(\lambda) \cdot C_{Hb}(x,y) \cdot L_{Hb}(x,y,\lambda)) + (\varepsilon_{Hbo}(\lambda) \cdot C_{Hbo}(x,y) \cdot L_{oHb}(x,y,\lambda)) \quad (6)$$

$A_{POL}$ isolates the absorption of deep melanin, oxy- and deoxy hemoglobin thereby simplifying the quantification of these components. The term "deep" refers to light penetration into the reticular dermis to a depth of approximately 300 µm or more. In order to simplify the regression analysis to a linear regression problem and avoid adding nonlinear complexity, the pathlengths for the deep layer (dermis) are assumed to be equal for both deep melanin and hemoglobin ($L_{m-d} \approx L_{Hb} \approx L_{oHb}$). This approximation limits the system to extracting only relative concentration differences in spatial maps but nevertheless provides diagnostic utility.

3. Polarized Hyperspectral Data for Skin Having a Melanocytic Nevus and Skin Having Vitilgo Color images of skin with a melanocytic nevus and with vitiligo, in both parallel and cross polarization modes, are shown in FIGS. 17(a) and 17(b) and FIGS. 17(e) and 17(f), respectively. The cross polarization images show how the superficial and specular reflectance from the air-tissue interface is reduced and how more subsurface details (such as lesion boundary, micro-vascular patterns) become visible compared to the parallel polarization images. The cross-polarized optical density spectrum ($OD_\perp$), defined herein as the negative logarithm of calibrated reflectance image stacks $Z_\perp$ is shown in FIGS. 17(c) and 17(g) next to the polarized attenuation spectrum $A_{POL}$ shown in FIGS. 17(d) and 17(h), respectively for melanocytic nevus and vitiligo.

The optical density spectra ($OD_\perp$) and the polarized attenuation spectra ($A_{POL}$), as described in Eq. (5) are taken from three regions of interest: (central region) the melanocytic nevus core, (boundary region) halo, and surrounding normal skin. The optical density spectrum ($OD_\perp$ of the melanocytic nevus core (red square) shows the highest overall spectrum optical density (red line) due to its high melanin concentration. As shown in FIG. 17(d), the relatively strong melanin contribution in the melanocytic nevus core results in a high polarized attenuation ($A_{POL}$).

The opposite attenuation trend in the skin exhibiting vitiligo is demonstrated in FIG. 17(h). Both the $OD_\perp$ and $A_{POL}$ spectra show the absence of melanin in the area with vitiligo. Consequently, oxy-hemoglobin (oHb) and deoxy hemoglobin (Hb) attenuation are the primary contributors to the skin absorption feature.

By comparing the $A_{POL}$ and $OD_\perp$ spectra, it can be seen that the slopes of these lines between 615 nm and 670 nm are correlated with the expected melanin concentration. For example, as shown in FIG. 17(d), the slope of the attenuation spectrum in the melanocytic nevus core area (red lines) is steeper compared to the surrounding normal skin (green lines).

4. Polarized Hyperspectral Data Illustrating the Effects of Melanin Masking

An occlusion condition was induced by a plastic cuff on an imaged finger. A time sequence of 300×150 pixels images from the same field of view at the dorsal side of the finger were cropped and concatenated to form a photographic strip chart shown, before putting on the cuff, during occlusion, and after removal of the cuff. The images were taken at thirty second intervals. The same experiment was repeated with the same subject's hand while probing the volar-side of the finger.

FIGS. 18(a) and 18(b) are color images of a portion of skin on the dorsal side of a subject's finger during application of occlusion captured under parallel and close polarization illumination respectively. FIGS. 18(e) and 18(f) show color images of the volar side captured by parallel and cross polarization cameras, respectively. The volar side of the finger usually has less melanin concentration compared to the dorsal side of the finger. The darker color images during occlusion are caused by higher hemoglobin absorption due to more blood pooling in superficial blood vessels. Image contrast in cross polarization mode is enhanced due to the rejection of specular and superficial reflectance and preferentially selecting deeper penetrating light.

Comparing the dorsal and volar sides of the subject's finger reveals the effect of hemoglobin variations (both oHb and Hb) in two skin locations with different amounts of melanin. The volar side of the finger usually has a lower melanin concentration. The color images clearly show that there is more attenuation due to blood accumulation in superficial blood vessels during the occlusion. The image contrast has been enhanced by imaging through crossed polarizers which reject the specular and superficial reflectance, which contribute little information regarding the subsurface skin composition.

FIGS. 18(c) and 18(d) also show the optical density ($OD_\perp$) and polarized attenuation ($A_{POL}$) spectra from three representative images before, during, and after occlusion for the dorsal side of the finger. FIGS. 18(g) and 18(h) show the optical density $OD_\perp$ and polarized attention $A_{POL}$ for three corresponding images before, during and after occlusion for the volar side of the finger. Both $OD_\perp$ and $A_{POL}$ spectra of both sides show higher attenuation during the occlusion period due to increased blood volume. During occlusion, the shape of attenuation spectra in the 500 nm-600 nm range more closely matches the single absorption peak of deoxy-hemoglobin absorption spectrum as compared to the two absorption peaks of oxy hemoglobin. This change in absorption trend is a result of progressive deoxygenation of the trapped blood due to the occlusion.

The optical density spectra ($OD_\perp$) and polarized attenuation spectra ($A_{POL}$) show an increase in magnitude in the 500 nm-600 nm range. In addition, there is a change in the absorption peak shape (related to hemoglobin). These changes are similar for both the dorsal and volar sides of the finger during the occlusion period. In the graphs of the spectra each solid line represents the mean of the corresponding pixel area (10×10 pixels) shown in the related color images. The error bars represents the standard deviation of the attenuation at each wavelength for the pixels in the designated areas. While, the boxes in the color images appear to be from slightly different locations but are actually from the same anatomical location. The position change is due to slight movement of the finger during data acquisition.

5. Hemoglobin Quantification Method

Figure 19:
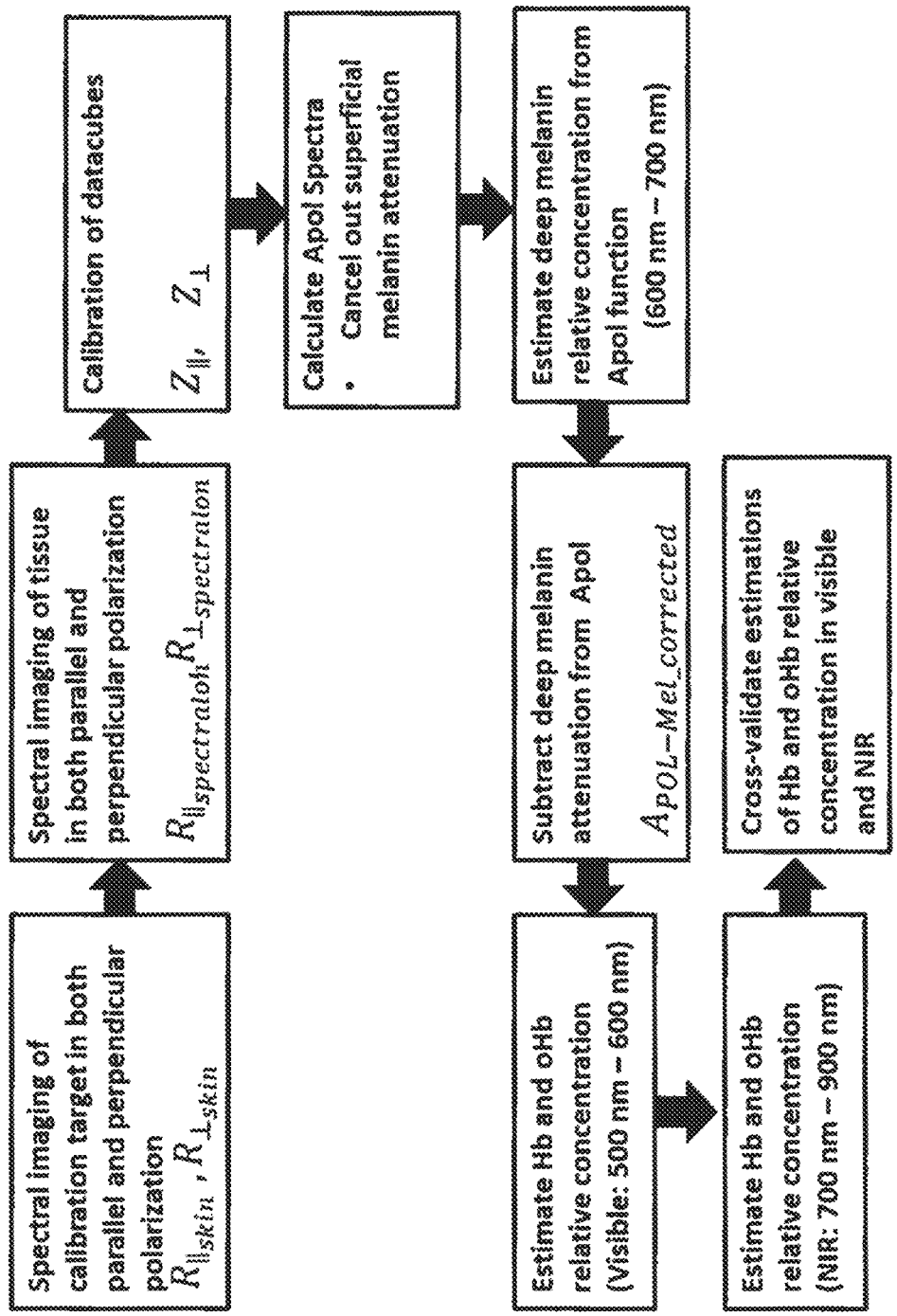
FIG. 19 is a flow chart of a process for estimating the quantity of hemoglobin to characterize a tissue anomaly.

The overall process for the quantifying of hemoglobin for determining of a coefficient is shown in FIG. 19.

Oxy-hemoglobin has two absorption coefficient maxima at 542 nm and 574 nm wavelengths and deoxy-hemoglobin exhibits a single absorption coefficient maximum at 545 nm. Melanin has a steadily linearly decreasing absorption trend in the spectral range from 600-700 nm and the slope of this curve increases proportional to the melanin content of an individual's skin Kollias, N, & Baqer, A., On the assessment of melanin in human skin in vivo, *Photochem Photobiol*, 43, 49-54 (1986). Light absorption by melanin and hemoglobin are similar in magnitude at wavelengths between 500-580 nm and hemoglobin or melanin concentration changes can be confused with one another during linear regression analysis.

Instead, both oxy- and deoxy-hemoglobin absorption drops by one to two orders of magnitude at wavelengths longer than 600 nm, while the melanin absorption is still strong. The slope of the $A_{POL}$ function from 615 nm to 670 nm can be correlated with the concentration of deep melanin and is less affected by the influence of hemoglobin absorption. Therefore the deep melanin spatial distribution, $Mel_d$ (x,y), can be estimated as:

$$Mel_d(x,y) = A_{POL}(x,y,615 \text{ nm}) - A_{POL}(x,y,670 \text{ nm}) \quad (7)$$

The $A_{POL}$ function can be corrected for the deep melanin absorption determined between 615 nm and 670 nm. The corrected spectrum $A_{POL\text{-}Mel\ corrected}$ can be analyzed to determine the oxy- and deoxy-hemoglobin concentrations using the linear least-square regression analysis in the 500 nm-577 nm wavelength range (7 wavebands). This range encompasses the local absorption spectrum maxima of both oxy- and deoxy-hemoglobin. The resulting two-dimensional hemoglobin maps enable visualization of the superficial capillary network, as well as venous and arterial plexi, which are independent of melanin variations.

6. Image Analysis for Skin Compositional Mapping

FIGS. 20(*a*)-20(*h*) show the derived chromophore maps of the skin with a melanocytic nevus FIGS. 18(*a*)-18(*d*) as well as skin with vitiligo FIGS. 18(*e*)-18(*h*). The skin melanin maps FIGS. 18(*b*) and 18(*f*) were calculated from the optical density spectra ($OD_\perp$) in cross-polarization mode. For relative melanin estimation, a three-chromophore model was used, including melanin, oxy-hemoglobin and deoxy-hemoglobin employing curve-fitting algorithms with the extinction coefficients of the chromophores as primary vectors. FIG. 18(*c*) shows how high melanin concentration is conducive to misestimation of the hemoglobin concentrations. The deep melanin estimation method described above was applied to correct this hemoglobin misestimation. FIG. 18(*d*) shows how this approach corrects the hemoglobin over-estimation in the nevus. The melanin corrected polarized attenuation spectrum ($A_{POL\text{-}Mel\_corrected}$) was employed for hemoglobin estimation using a two-chromophore (oHb and Hb) model and curve-fitting algorithms with the extinction coefficients of oHb and Hb as primary vectors in the 500 nm-577 nm spectral range.

Total hemoglobin was calculated by the summation of oxy-hemoglobin and deoxy-hemoglobin. The oxygenation saturation parameter (OSP) was calculated as a ratio of oxy-hemoglobin by the total hemoglobin as a percentage. By comparing FIG. 18(*c*) and FIG. 18(*d*), it is clear that without the melanin correction step, the skin area with a strong melanin contribution leads to the hemoglobin over-estimation, FIG. 18(*c*) while melanin correction causes the biologically implausible melanin-related hemoglobin artifact to be nearly eliminated, FIG. 18(*b*).

Chromophore maps of skin with vitiligo were derived to evaluate the efficiency of the algorithm in skin tissue lacking melanin. The relative melanin distribution map for areas with vitiligo, FIG. 20(*f*) matched expectations for melanin. Without correction of melanin-hemoglobin effect, the estimated oxy- and deoxy-hemoglobin shows high correlation with melanin in vitiligo, the same effect shown in highly pigmented nevus, FIG. 20(*g*). By applying the same melanin correction method to the $A_{POL}$ spectrum, the same correction effect in the areas with vitiligo was confirmed, providing a more biologically plausible hemoglobin distribution, FIG. 18(*h*). By comparing the melanin correction effect on hemoglobin distribution, the melanocytic nevus is more strongly affected due to the greater melanin difference to the surrounding normal skin then when the correction is observed for the vitiligo condition.

Figure 21A:
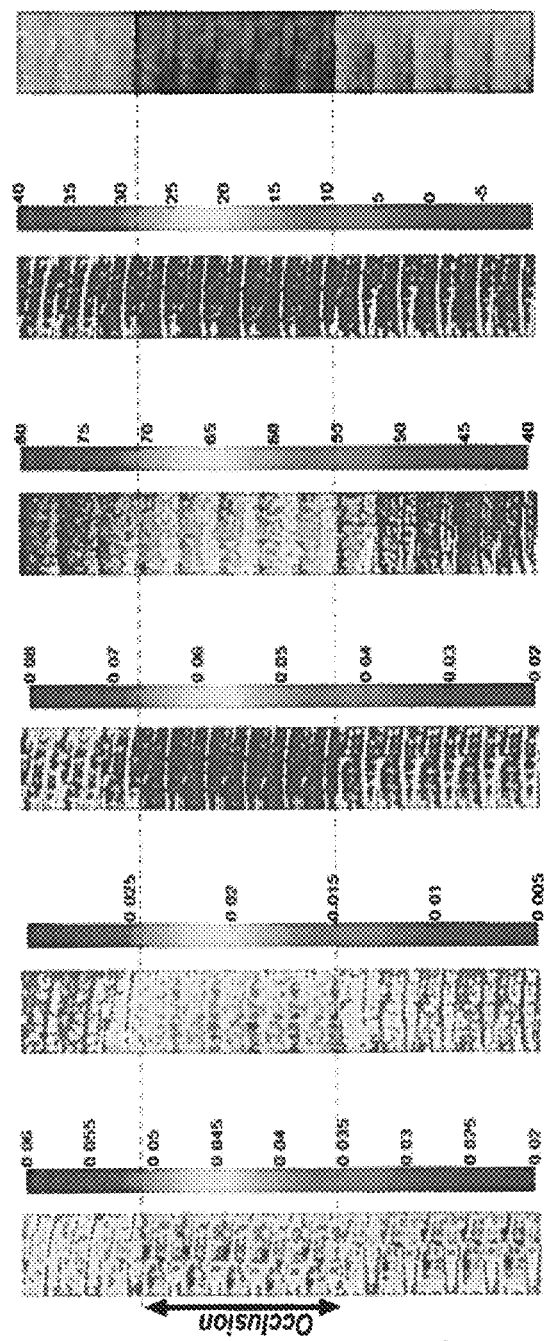
FIG. 21(a) is a Relative molar absorptivity of Oxy-hemoglobin (oHb), deoxy-hemoglobin (Hb), total hemoglobin (tHb), melanin and oxygen saturation (OSP) maps with corresponding color cross-polarized image of dorsal finger during finger cuff occlusion.
Figure 21B:
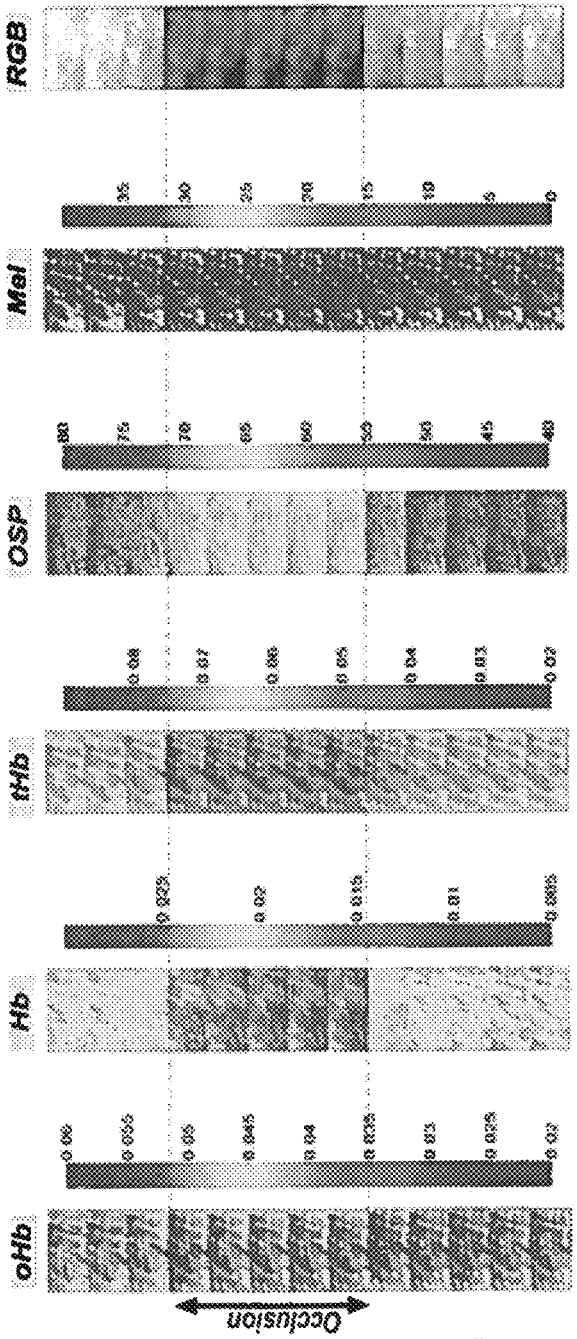
FIG. 21(b) is a Relative molar absorptivity of Oxy-hemoglobin (oHb), deoxy-hemoglobin (Hb), total hemoglobin (tHb), melanin and oxygen saturation (OSP) maps with corresponding color cross-polarized image of volar finger during finger cuff occlusion.

To illustrate the efficiency of the skin chromophore estimation algorithm for skin with blood flow variations and/or ischemia, FIG. 21 compares the cross-polarized color images and skin chromophore map sets for the dorsal-side and volar-side of a human finger during venous occlusion. The melanin corrected polarized attenuation spectra was from a region of interest (100×150 pixels) and fitted to a two chromophore skin model (oHb and Hb) in the 500 nm-577 nm range. The deep melanin estimation was the same method that was presented for nevus and vitiligo described in a previous section of this manuscript. During venous occlusion, the oxygen saturation decreases, while the blood volume and deoxy hemoglobin concentrations increase Tsumura, N., Kawabuchi, M., Haneishi, H., & Miyake, Y. Mapping pigmentation in human skin from a multi-channel visible spectrum image by inverse optical scattering technique, *J. Imaging Sci. Technol.*, 45, 444-450 (2001). We are aware that the cuff pressure can change the venous occlusion into venous and arterial occlusion state which results in different oxy and deoxy characteristics Tsumura, N., Kawabuchi, M., Haneishi, H., & Miyake, Y. Mapping pigmentation in human skin from a multi-channel visible spectrum image by inverse optical scattering technique, *J. Imaging Sci. Technol.*, 45, 444-450 (2001). The deep melanin does not change during, before and after occlusion, as expected. The algorithm presented here and applied to pigmented lesions is effective for relative oxygenation saturation and total blood concentration estimation since results that were obtained for dorsal and volar sides of a finger (with different melanin contents) agree with the physiological values for oxygenation percentage (OSP) of around 65% during the occlusion and about 80% during perfusion as shown by other researchers. Zuzak, K. J., Schaeberle, M. D., Lewis, E.

N., & Levin, I. W. Visible reflectance hyperspectral imaging: characterization of a noninvasive, in vivo system for determining tissue perfusion, *Anal Chem,* 74, 2021-2028 (2002) Matthijs, D., Hondebrink, E., van Leeuwen, T., & Steenbergen, W. Time domain algorithm for accelerated determination of the first order moment of photo current fluctuations in high speed laser Doppler perfusion imaging, *Med Bio Eng Comp,* 47, 1103-1109 (2009).

7. Data Acquisition

To analyze the effect of melanin on hemoglobin oxygenation quantification, two volunteer subjects were selected, one with a melanocytic nevus and the other with skin exhibiting vitiligo, both on the subjects' arms. To analyze the effect of hemoglobin oxygenation variation on melanin quantification by venous occlusion the volunteers were seated in a comfortable position during data acquisition in order to minimize artifacts due to subject movement.

For the occlusion measurements, three measurements of the subject's finger were initiated before initiating occlusion (by a plastic cuff on subject's finger). Five post-occlusion measurements were taken, then another five measurements after cuff removal (during reperfusion). All data were taken at 30 second intervals. Two sets of measurements, one from the volar surface of the finger and the other from the dorsal surface of the finger were acquired. This permitted a comparison of the effect of melanin change on tissue oxygenation estimation as the volar side of the finger had less melanin. Vyas, S., Banerjee, A., & Burlina, P. Estimating physiological skin parameters from hyperspectral signatures., *J Biomed Opt,* 18, 057008 (2013).

The terms and expressions which have been employed in the foregoing specification are used therein as terms of description and of limitation, and there is no intention, in the use of such terms and expressions, to exclude equivalents of the features shown and described or portions thereof, it being recognized that the scope of the invention is defined and limited only by the claims that follow.

The invention claimed is:

1. A method of characterizing biological tissue, comprising:
    illuminating tissue in vivo with a temporal sequence of multiple wavelengths of polarized light comprising a continuum between 400 nm and 1000 nm;
    separating light emitted from said tissue in response to said illumination into at least two polarization components, wherein the at least two polarization components comprise different linear polarizations of the separated light, and are captured using parallel and cross orientations of a polarizing filter in a detection path with respect to an orientation of a second polarizing filter in an illumination path used to illuminate the tissue;
    calculating a degree of linear polarization of the light emitted from said tissue based on measurements of an intensity for each of the at least two polarization components of the emitted light, respectively;
    forming at least two respective hyperspectral image sets from said at least two polarization components;
    identifying a distribution of superficial melanin in an illuminated portion of the tissue and cancelling a contribution of the superficial melanin in one or more images in the hyperspectral image sets, and thereafter estimating an amount of oxyhemoglobin, deoxyhemoglobin, or both oxyhemoglobin and deoxyhemoglobin, in the tissue, wherein superficial melanin is melanin between the surface of the skin and 120 μm depth;
    generating a three-dimensional model of the tissue comprising an array of individual tissue-characteristic three-dimensional voxels based on the degree of linear polarization of the emitted light as a function of wavelength and position in measurement space; and
    determining at least one characteristic of said tissue.

2. The method of claim 1, wherein the light emitted from the tissue comprises one or more of reflected light, scattered light and fluorescence light, whose intensities form a multimode image dataset.

3. The method of claim 1, wherein the at least one characteristic of said tissue that is determined is a three-dimensional quantitative spatial distribution of melanin, oxyhemoglobin, deoxyhemoglobin and/or collagen in the illuminated portion of the tissue.

4. The method of claim 3, further comprising identifying a distribution of deep melanin in the illuminated portion of tissue and cancelling a contribution of the deep melanin in the one or more images in the hyperspectral image sets prior to estimating the amount of oxyhemoglobin, deoxyhemoglobin, or both oxyhemoglobin and deoxyhemoglobin, in the illuminated portion of tissue, wherein the deep melanin corresponds to a melanin having a depth larger than 120 μm from a surface of the tissue.

5. The method of claim 1, further comprising measuring the intensity for each of the at least two polarization components of the emitted light respectively.

6. The method of claim 1, wherein the at least one characteristic of the tissue that is determined is a three-dimensional quantitative spatial distribution of melanin, oxyhemoglobin, deoxyhemoglobin and collagen in the illuminated portion of the tissue.

* * * * *